United States Patent
Shrivastava et al.

(10) Patent No.: US 11,326,210 B2
(45) Date of Patent: May 10, 2022

(54) COMPOSITIONS AND METHODS FOR MONITORING, DIAGNOSIS, PROGNOSIS, DETECTION, AND TREATMENT OF CANCER

(71) Applicant: GLAX LLC, Wilmington, DE (US)

(72) Inventors: Shivani Shrivastava, Wilmington, DE (US); Rakesh K Srivastava, Tyler, TX (US)

(73) Assignee: GLAX LLC, Wilmington, DE (US)

( * ) Notice: Subject to any disclaimer, the term of this patent is extended or adjusted under 35 U.S.C. 154(b) by 0 days.

(21) Appl. No.: 15/547,069

(22) PCT Filed: Feb. 1, 2016

(86) PCT No.: PCT/IB2016/050495
§ 371 (c)(1),
(2) Date: Jul. 28, 2017

(87) PCT Pub. No.: WO2016/120853
PCT Pub. Date: Aug. 4, 2016

(65) Prior Publication Data
US 2018/0010195 A1    Jan. 11, 2018

Related U.S. Application Data

(60) Provisional application No. 62/110,153, filed on Jan. 30, 2015.

(51) Int. Cl.
| | |
|---|---|
| *C07H 21/04* | (2006.01) |
| *C07H 21/02* | (2006.01) |
| *C12Q 1/6886* | (2018.01) |
| *G01N 33/574* | (2006.01) |
| *A61K 31/7052* | (2006.01) |
| *C12Q 1/6883* | (2018.01) |
| *A61K 31/713* | (2006.01) |
| *A61K 45/06* | (2006.01) |
| *C12N 15/113* | (2010.01) |

(52) U.S. Cl.
CPC ........ *C12Q 1/6886* (2013.01); *A61K 31/7052* (2013.01); *A61K 31/713* (2013.01); *A61K 45/06* (2013.01); *C12Q 1/6883* (2013.01); *G01N 33/57407* (2013.01); *G01N 33/57496* (2013.01); *C12N 15/113* (2013.01); *C12N 2310/11* (2013.01); *C12N 2310/14* (2013.01); *C12N 2310/141* (2013.01); *C12N 2320/30* (2013.01); *C12Q 2600/106* (2013.01); *C12Q 2600/112* (2013.01); *C12Q 2600/158* (2013.01); *G01N 2333/4703* (2013.01); *G01N 2800/7095* (2013.01)

(58) Field of Classification Search
CPC .......................... A61K 31/713; C12N 2310/14
See application file for complete search history.

(56) References Cited

U.S. PATENT DOCUMENTS

| | | | |
|---|---|---|---|
| 8,912,159 B2* | 12/2014 | Iragavarapu-Charyulu | G01N 33/6893 514/44 A |
| 2013/0296403 A1* | 11/2013 | Donald | A61K 31/138 514/44 A |

FOREIGN PATENT DOCUMENTS

| | | | | |
|---|---|---|---|---|
| WO | WO 2004/069991 | * | 8/2004 | C12N 15/113 |

OTHER PUBLICATIONS

Martin et al. (Oncogene, 2005, vol. 24, pp. 6890-6901).*
Patani et al. (CancerCell International, 2009, 9: 18, pp. 1-10).*
Wang et al. (Journal of Pathology, 2009, 219, 114-122).*
Killick E. et al. Role of Engrailed-2 (EN2) as a prostate cancer detection biomarker in genetically high risk men, Scientific Reorts, 2013, vol. 3, 2059, DOI: 10.1038/srep02059, p. 1-5.
Martin N.L. et al. EN2 is a candidate oncogene in human breast cancer, Oncogene, 2005, vol. 24 pp. 6890-6901.
Stathopoulou A. et al. Molecular Detection of Cancer Cells in the Peripheral Blood of Patients with Breast Cancer: Comparison of CK-19, CEA and Maspin as Detection Markers, Anticancer Research, 2003, vol. 23. pp. 1883-1890.
Coussens L. M. et al. Inflammation and cancer, Nature, 2002, vol. 420, N.6917, p. 860-867. doi:10.1038/nature01322, p. 1-18.

* cited by examiner

*Primary Examiner* — Amy H Bowman

(57) ABSTRACT

The present invention relates to the field of cancer and inflammation, and in particular methods of monitoring, diagnosis, prognosis, detecting, treating and preventing cancer and inflammation conditions. The use of composition comprises method of monitoring, diagnosis, prognosis, and detecting cancer and inflammation with EN2 and/or SATB2 expression and/or activity. The pharmaceutical composition will further comprise agents that inhibit EN2 and/or SATB2 expression or activity.

5 Claims, 13 Drawing Sheets

COMPOSITIONS AND METHODS FOR MONITORING, DIAGNOSIS, PROGNOSIS, DETECTION, AND TREATMENT OF CANCER

CROSS REFERENCE TO RELATED APPLICATIONS

This application claims the benefit of U.S. Provisional Appl. No. 62/110,153, filed Jan. 30, 2015, the content of which is incorporated by reference herein in its entirety.

FIELD OF THE INVENTION

The present invention relates generally to the field of cancer and inflammation, and in particular methods of monitoring, diagnosis, prognosis, detecting, treating and preventing cancer and inflammation conditions.

More specifically, the present invention relates to the use of compositions for monitoring, diagnosis, prognosis, detecting, treating and preventing a cancer condition in a subject. The use of composition comprises method of monitoring, diagnosis, prognosis, and detecting cancer and inflammation with EN2 and/or SATB2 expression and/or activity. The pharmaceutical composition will further comprise agents that inhibit EN2 and/or SATB2 expression or activity.

BACKGROUND OF THE INVENTION

Cancer is a condition defined as uncontrolled cell growth, malignant transformation, having cancer stem cell characteristics, and able to maintain pluripotency, and stemness, and resistant to therapy.

Cancer is a deadly disease which can be detected in many ways, including the presence of certain signs and symptoms, screening tests, or medical imaging. Signs of cancer can be found in the blood, plasma, exosomes, body fluids, urine and tissues. One or multiple biomarkers can be used for monitoring, detection, diagnosis, treatment and assessing response to therapy. Proteins and RNA based biomarkers can be used.

Anticancer agents such as antisense, antibodies, oligonucleotides, shRNA, siRNA, natural products, and small organic molecules can be used to treat various types of cancer. Anticancer agents can be delivered in nanoparticles with targeting agents.

One aspect of the present application relates to a method of monitoring, diagnosis, and detecting cancer and inflammation with EN2 and/or SATB2 expression and/or activity. Another aspect of the present application relates to a method for treating a cancer condition in a subject, comprising: administering to the subject an effective amount of a pharmaceutical composition comprising agents that inhibit Engrailed-2 (EN2) expression and/or EN2 activity; and special AT-rich binding protein-2 (SATB2) expression and/or SATB2 activity.

Another aspect of the present application relates to method of delivering EN2 and/or SATB2 inhibitors in nanoparticles or nano-structures (synthetic or biological materials) conjugated with or without targeting and/or imaging agents.

(D), Transwell invasion assay was performed in breast CSCs/Scrambled and breast CSC/SATB2 shRNA groups. Data represent mean±SD. *=significantly different at P<0.05. (E), Transwell migration assay was performed in breast CSCs/Scrambled and breast CSC/SATB2 shRNA groups. Data represent mean±SD. *=significantly different at P<0.05.

Figure 1:
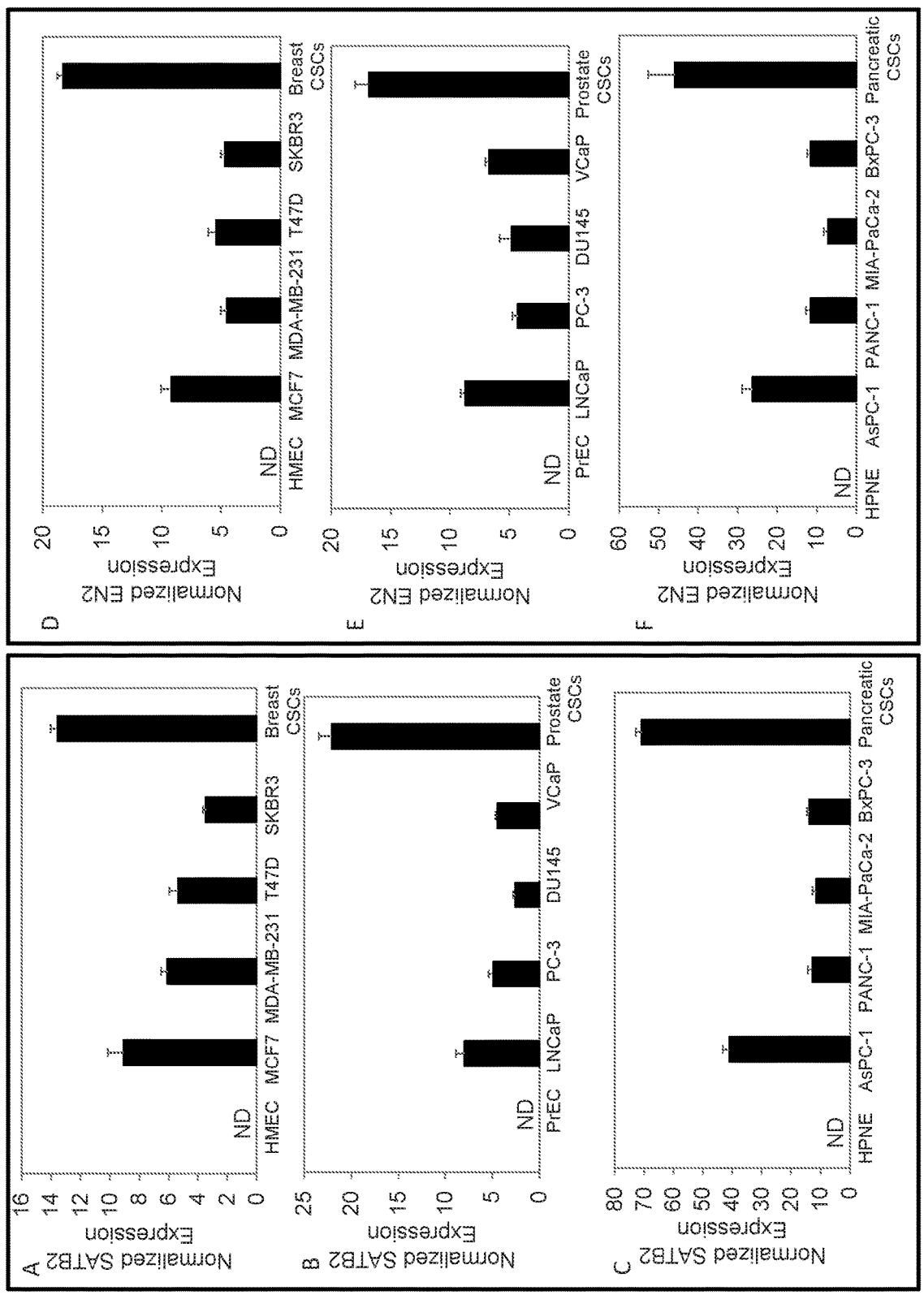
FIG. 1. SATB2 and EN2 are highly expressed in breast, prostate and pancreatic cancer cell lines and cancer stem cells (CSCs), but not in their respective normal cells. (A), Expression of SATB2 mRNA in human normal breast mammary epithelial cells (HMEC), breast cancer cell lines (MCF-7, MDA-MB-231, T47D, and SKBR3) and breast CSCs. RNA was isolated and the expression of SATB2 was measured by q-RT-PCR. GAPDH was used as an internal control. Data represent mean (n=4)±SD. ND=not detected. (B), Expression of SATB2 mRNA in human normal prostate epithelial cells (PrEC), prostate cancer cell lines (LNCaP, PC-3, DU145, and VCaP) and prostate CSCs. RNA was isolated and the expression of SATB2 was measured by q-RT-PCR. (C), Expression of SATB2 mRNA in human pancreatic normal ductal epithelial cells (HPNE), pancreatic cancer cell lines (AsPC-1, PANC-1, MIA-PaCa-2, and BxPC-3) and pancreatic CSCs. (D), Expression of EN2 mRNA in HMEC, breast cancer cell lines (MCF-7, MDA-MB-231, T47D, and SKBR3) and breast CSCs. (E), Expression of EN2 mRNA in PrEC, prostate cancer cell lines (LNCaP, PC-3, DU145, and VCaP) and prostate CSCs. (F), Expression of EN2 mRNA in HPNE, pancreatic cancer cell lines (AsPC-1, PANC-1, MIA-PaCa-2, and BxPC-3) and pancreatic CSCs. RNA was isolated and the expression of EN2 was measured by q-RT-PCR. GAPDH was used as an internal control. Data represent mean (n=4)±SD. ND=not detected.
Figure 2:
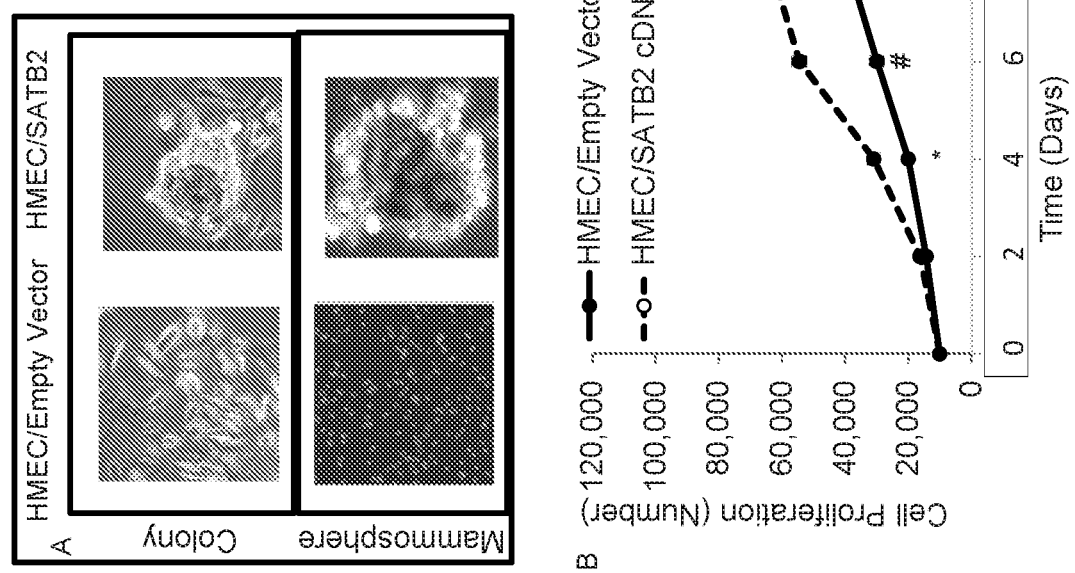
FIG. 2. Overexpression of SATB2 in HMECs induces cellular transformation and stemness. (A), Colony and mammosphere formation. HMECs were stably transduced with lentiviral particles expressing either empty vector or SATB2 cDNA. Colony and mammosphere formation by HMEC/Empty Vector and HMEC/SATB2 overexpressing cells were visualized by microscopy. Note, HMEC/empty vector cells did not form colony and mammosphere. Upper panel—colony; Lower panel=mammosphere. (B), Cell proliferation. HMEC/Empty Vector and HMEC/SATB2 cDNA cells were seeded in 6-well plates. Number of cells during 5-day period was counted by trypan blue assay. Data represent mean (n=4)±SD. *, #, and @=significantly different from HMEC/Empty Vector group, P<0.05.
Figure 3:
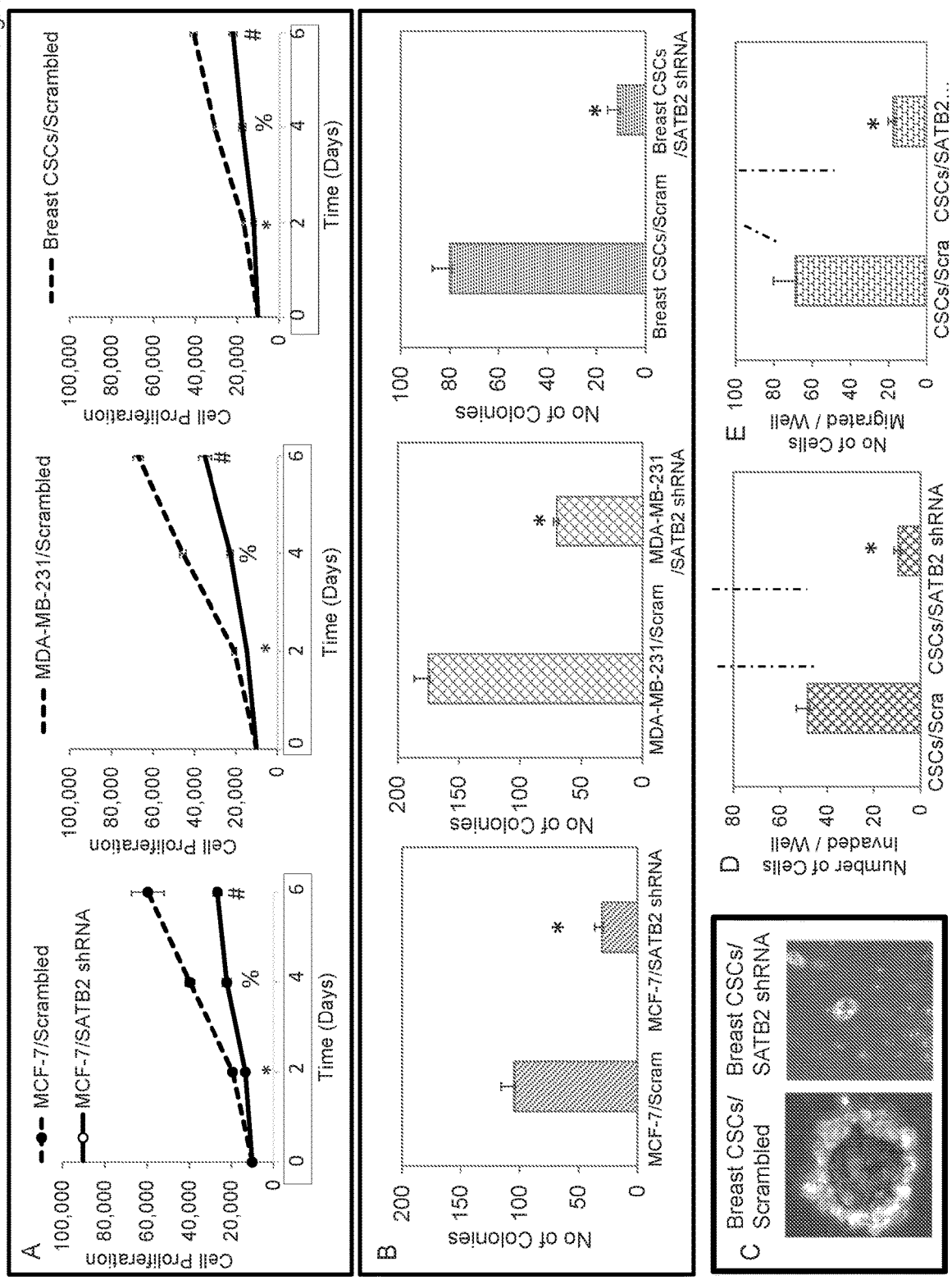
FIG. 3. SATB2 shRNA inhibits cell proliferation, colony formation, mammosphere formation, cell invasion and migration in breast cancer. (A), MCF-7, MDA-MB-231 and breast CSCs were transduced with lentiviral particles expressing either Scrambled or SATB2 shRNA. Cell proliferation of MCF-7/Scrambled, MDA-MB-231/Scrambled and Breast CSCs/Scrambled, MCF-7/SATB2 shRNA, MDA-MB-231/SATB2 shRNA and Breast CSCs/SATB2 shRNA groups was measured over 6-day period. (B), Colony formation Assay. MCF-7/Scrambled, MCF-7/SATB2 shRNA, MDA-MB-231/Scrambled, MDA-MB-231/SATB2 shRNA, Breast CSCs/Scrambled, and Breast CSCs/SATB2 shRNA cells were seeded, and number of colonies formed at 21 days were counted. Data represent mean (n=4)±SD. *=significantly different from Scrambled group (P<0.05). (C), Breast CSCs/Scrambled and breast CSCs/SATB2 shRNA cells were grown in suspension. After one week, photographs of mammospheres were taken.
Figure 4:
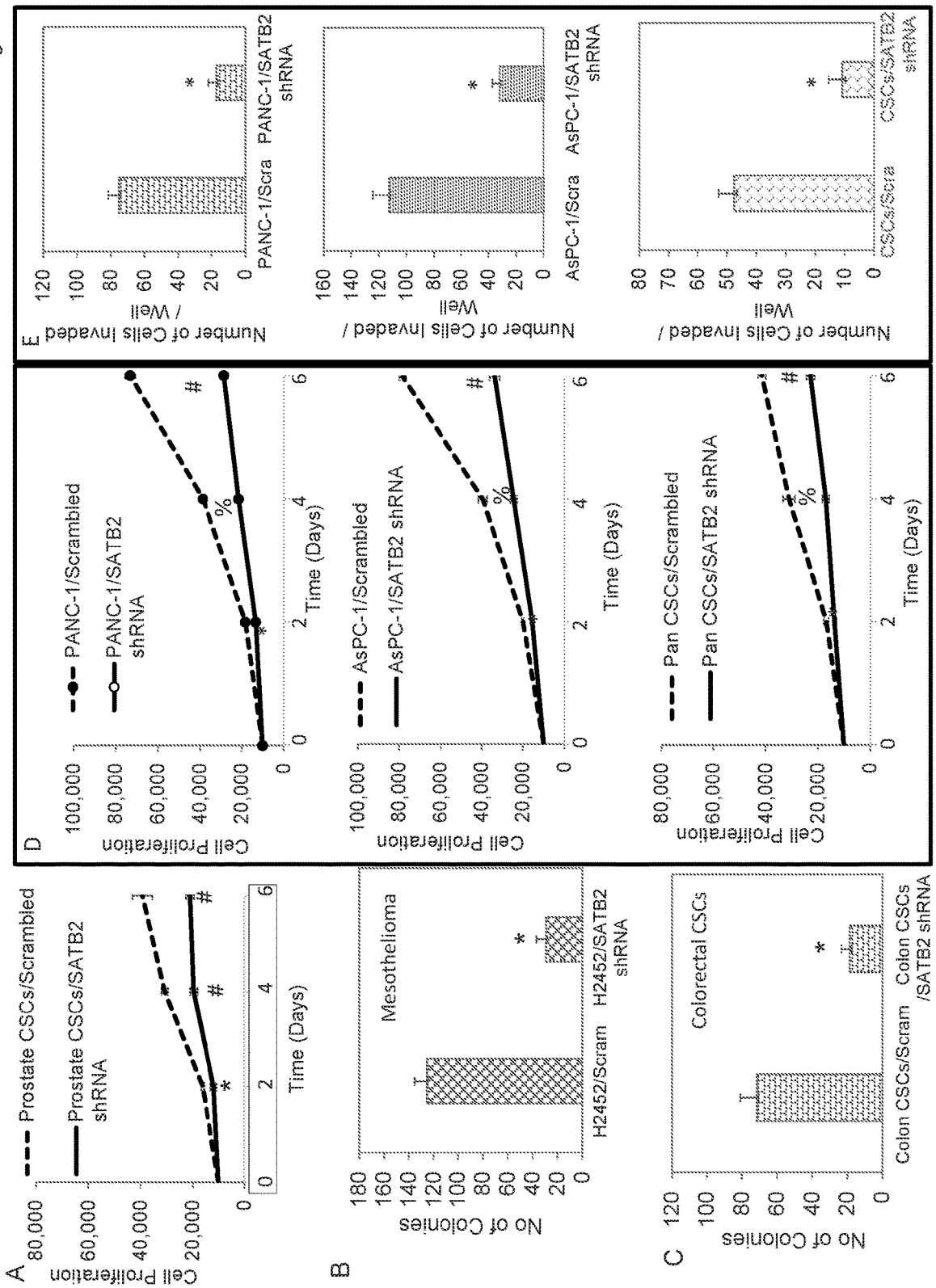

FIG. 4. Knockdown of SATB2 inhibits cell proliferation, colony formation and invasion in prostate cancer, mesothelioma, colon cancer and pancreatic cancer. (A), SATB2 shRNA inhibits prostate cancer stem cell (CSC) proliferation. Prostate CSCs were transduced with lentiviral particles expressing either Scrambled or SATB2 shRNA. Cell proliferation of Prostate CSCs/Scrambled, and Prostate CSCs/SATB2 shRNA groups was measured over 6-day period. Data represent mean (n=4)±SD. * or #=significantly different from Scrambled group (P<0.05). (B), SATB2 shRNA inhibits colony formation in mesothelioma. H2452/Scrambled, H2452/SATB2 shRNA, H2595/Scrambled, and H2595/SATB2 shRNA cells were seeded, and number of colonies formed at 21 days were counted. Data represent mean (n=4)±SD. *=significantly different from Scrambled group (P<0.05). (C) SATB2 shRNA inhibits colony formation in colorectal CSCs. Colorectal CSCs/Scrambled and Colorectal CSCs/SATB2 shRNA cells were seeded, and number of colonies formed at 21 days were counted. Data represent mean (n=4)±SD. *=significantly different from Scrambled group (P<0.05). (D), SATB2 shRNA inhibits cell proliferation in pancreatic cancer cell lines (PANC-1 and AsPC-1) and pancreatic CSCs. Cells were transduced with lentiviral particles expressing either Scrambled or SATB2 shRNA. Cell proliferation of Scrambled, and SATB2 shRNA groups was measured over 6-day period. Data represent mean (n=4)±SD. *, % or #=significantly different from Scrambled group (P<0.05). (E), SATB2 shRNA inhibits cell invasion. Pancreatic cancer cell lines (PANC-1 and AsPC-1) and pancreatic CSCs were transduced with lentiviral particles expressing either Scrambled or SATB2 shRNA, and transwell invasion assay was performed. Data represent mean±SD. *=significantly different at P<0.05.

Figure 5:
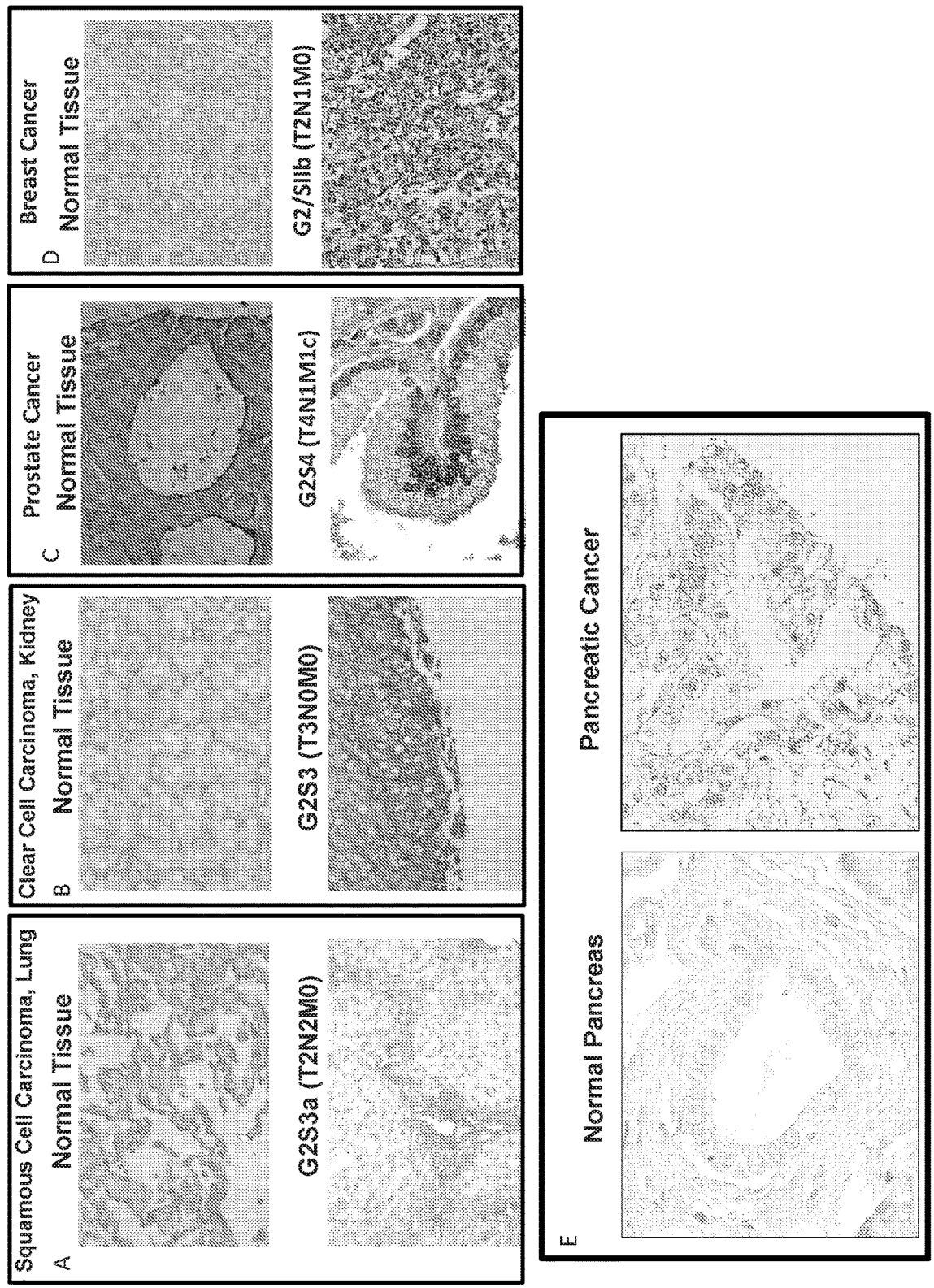

FIG. 5. SATB2 is highly expressed in human squamous cell carcinoma, clear cell carcinoma, prostate cancer, breast cancer and pancreatic cancer tissues, but not in their respective normal tissues. (A), Immunohistochemistry (IHC) was performed to measure the expression of SATB2 in lung normal and squamous cell carcinoma. N=10. (B), IHC was performed to measure the expression of SATB2 in kidney normal tissues and clear cell carcinoma. N=10. (C), IHC was performed to measure the expression of SATB2 in prostate normal tissues and prostate cancer tissues. N=10. (D), IHC was performed to measure the expression of SATB2 in breast normal and cancer tissues. N=10. (E) IHC was performed to measure the expression of SATB2 in pancreatic normal tissues and cancer tissues. Representative photograph of 10 pancreatic tissues.

Figure 6:
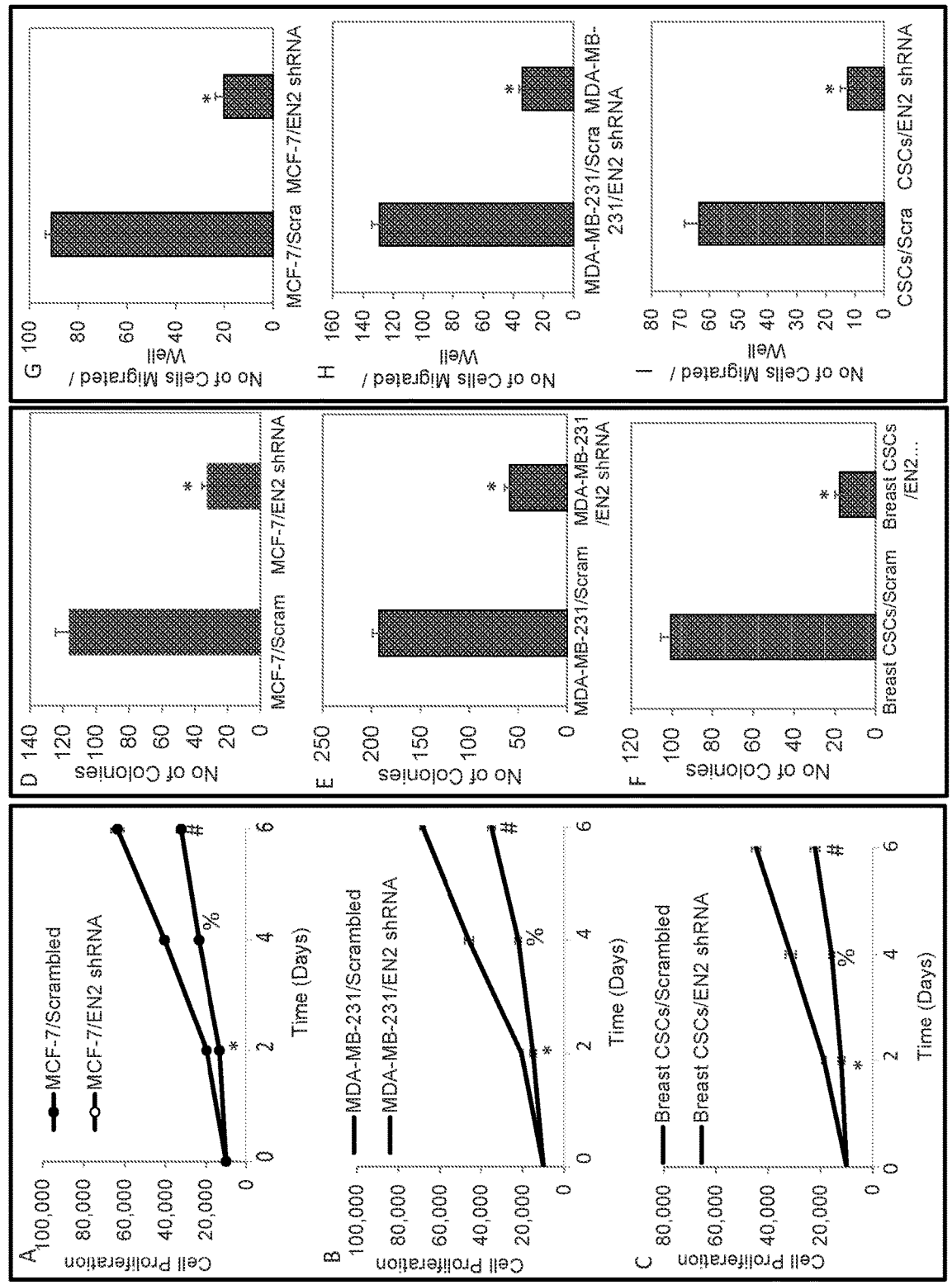

FIG. 6. EN2 shRNA inhibits cell proliferation, colony formation and cell migration in breast cancer cell lines and breast CSCs. (A-C), MCF-7, MDA-MB-231 and breast CSCs were transduced with lentiviral particles expressing either Scrambled or EN2 shRNA. Cell proliferation of MCF-7/Scrambled, MCF-7/EN2 shRNA, MDA-MB-231/Scrambled, MDA-MB-231/EN2 shRNA, CSCs/Scrambled and CSCs/EN2 shRNA was measured for 6-days. Data represent mean (n=4)±SD. *, % or #=significantly different from Scrambled group (P<0.05). (D-F), Colony formation Assay. MCF-7/Scrambled, MCF-7/EN2 shRNA, MDA-MB-231/Scrambled, MDA-MB-231/EN2 shRNA, CSCs/Scrambled and CSCs/EN2 shRNA were seeded, and number of colonies formed at 21 days were counted. Data represent mean (n=4)±SD. *=significantly different from Scrambled group (P<0.05). (G-I), Cell Migration Assay. MCF-7/Scrambled, MCF-7/EN2 shRNA, MDA-MB-231/Scrambled, MDA-MB-231/EN2 shRNA, CSCs/Scrambled and CSCs/EN2 shRNA were seeded, and cell migration assay was performed. Data represent mean (n=4)±SD. *=significantly different from Scrambled group (P<0.05).

Figure 7:
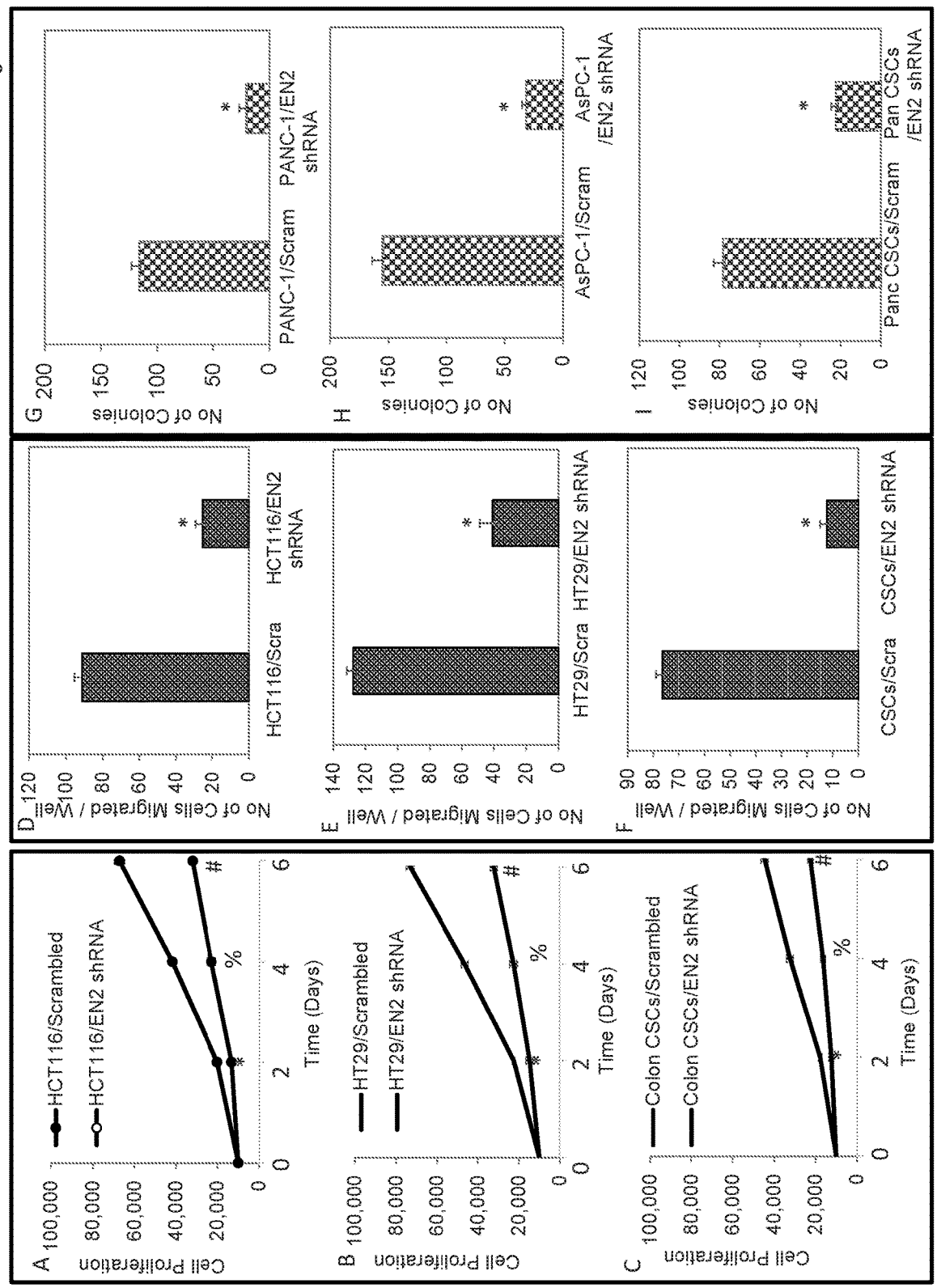

FIG. 7. EN2 shRNA inhibits cell proliferation, colony formation and cell migration in colorectal and pancreatic cancer cell lines, and cancer stem cells. (A-C), HCT116, HT29 and colorectal CSCs were transduced with lentiviral particles expressing either Scrambled or EN2 shRNA. Cell proliferation between Scrambled and EN2 shRNA groups was measured for 6-days. Data represent mean (n=4)±SD. *, % or #=significantly different from Scrambled group (P<0.05). (D-F), Cell Migration Assay. HCT116/Scrambled, HCT116/EN2 shRNA, HT29/Scrambled, HT29/EN2 shRNA, colorectal CSCs/Scrambled and colorectal CSCs/EN2 shRNA groups were seeded, and cell migration assay was performed. Data represent mean (n=4)±SD. *=significantly different from Scrambled group (P<0.05). (G-I), Colony formation Assay in pancreatic cancer. PANC-1/Scrambled, PANC-1/EN2 shRNA, AsPC-1/Scrambled, AsPC-1/EN2 shRNA, pancreatic CSCs/Scrambled and pancreatic CSCs/EN2 shRNA groups were seeded, and number of colonies formed at 21 days were counted. Data represent mean (n=4)±SD. *=significantly different from Scrambled group (P<0.05).

Figure 8:
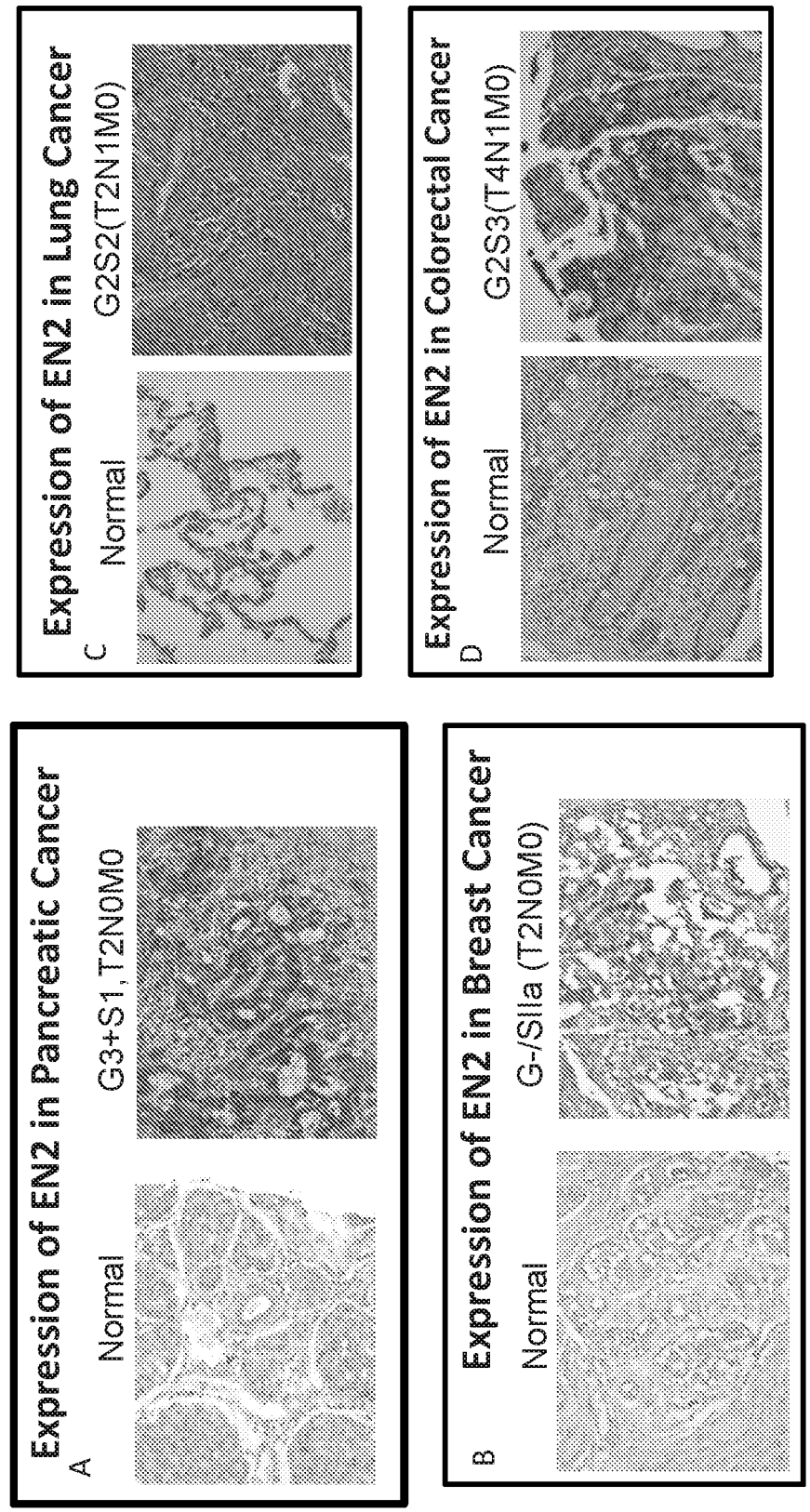
Figure 9:
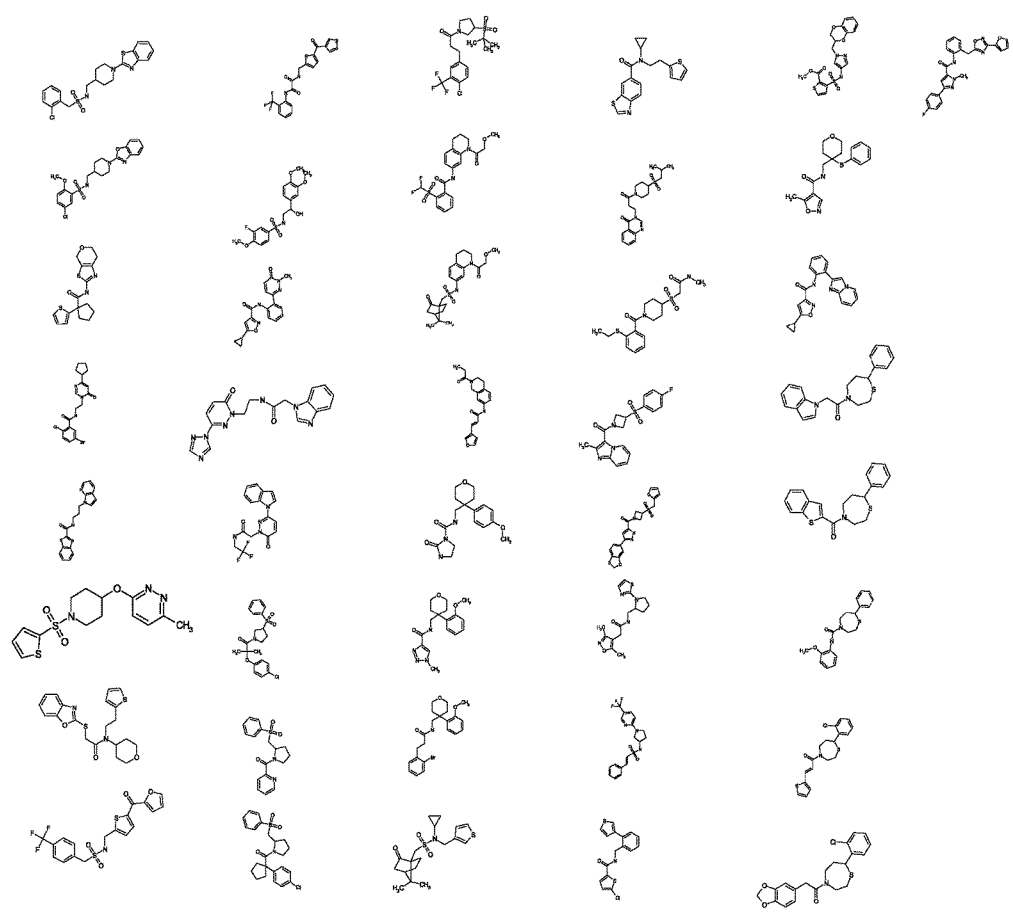
Figure 10:
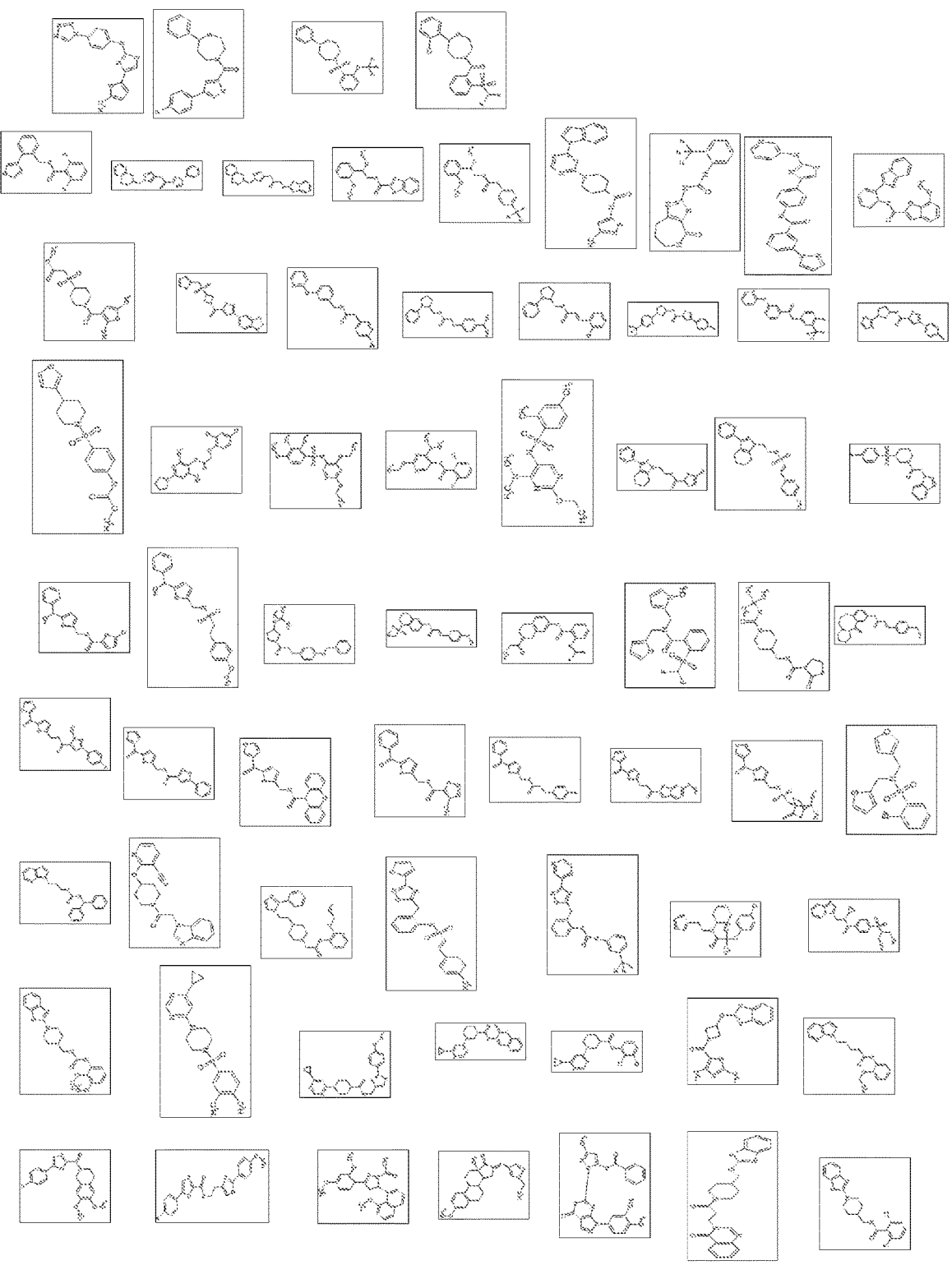
Figure 11:
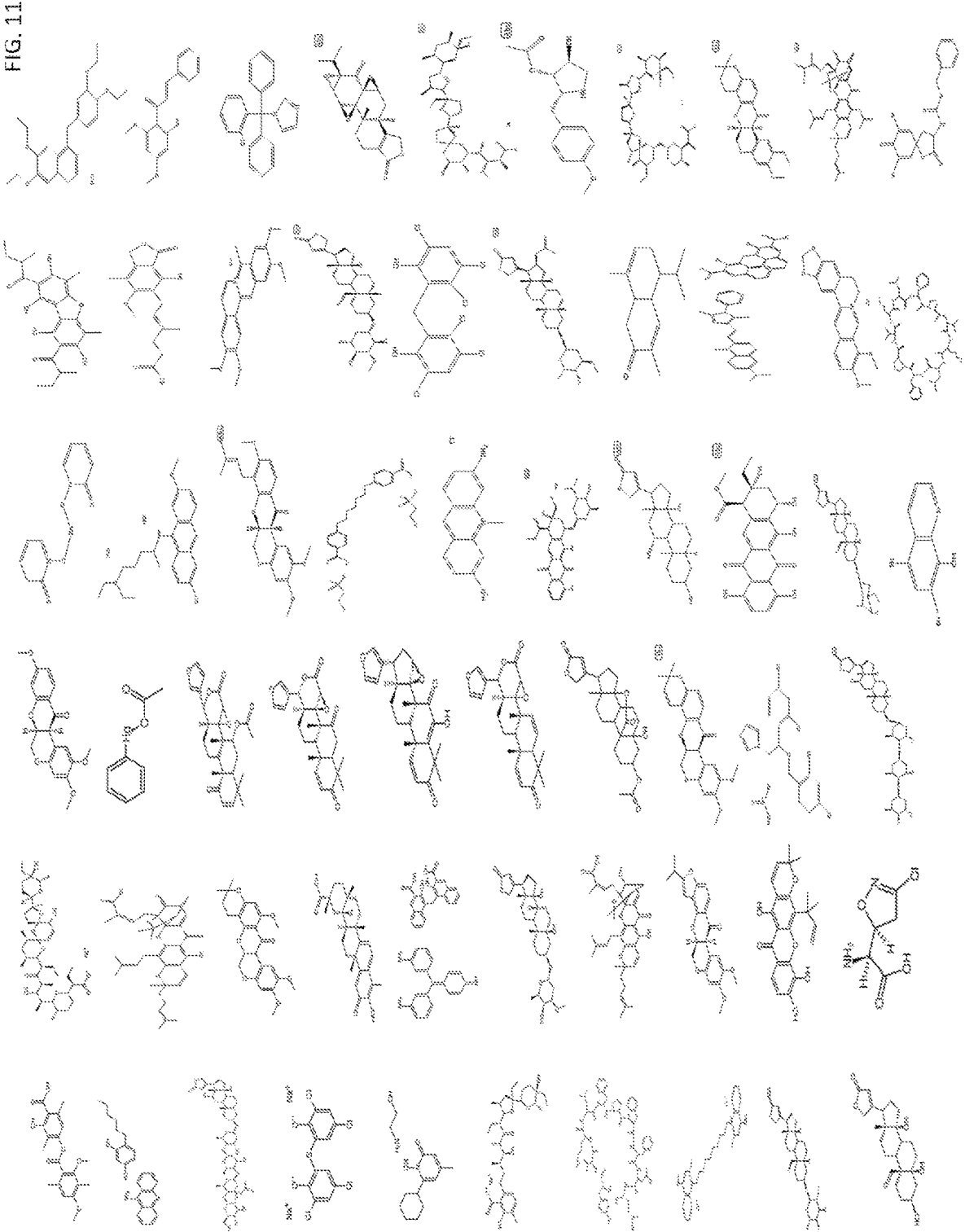
Figure 12:
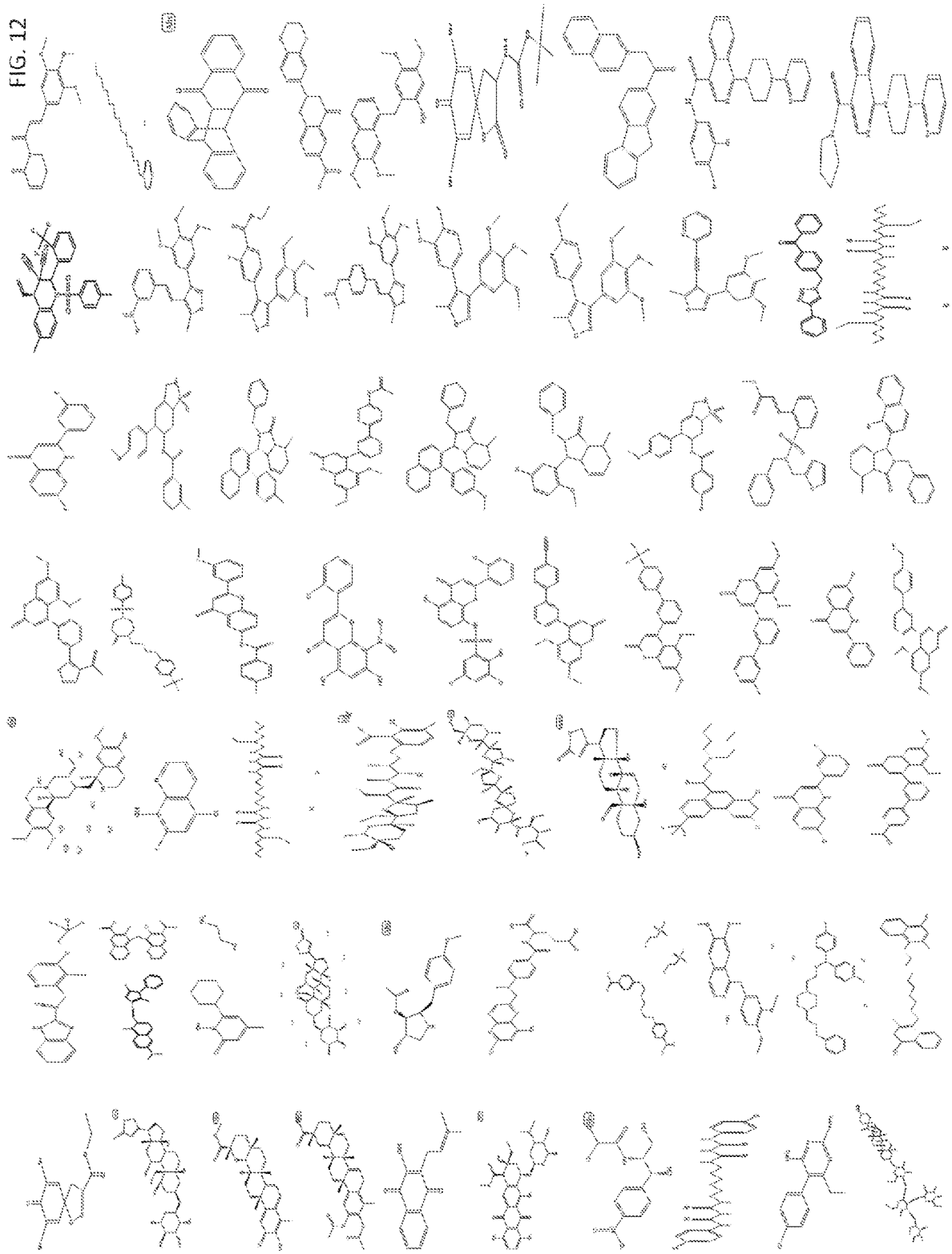
Figure 13:
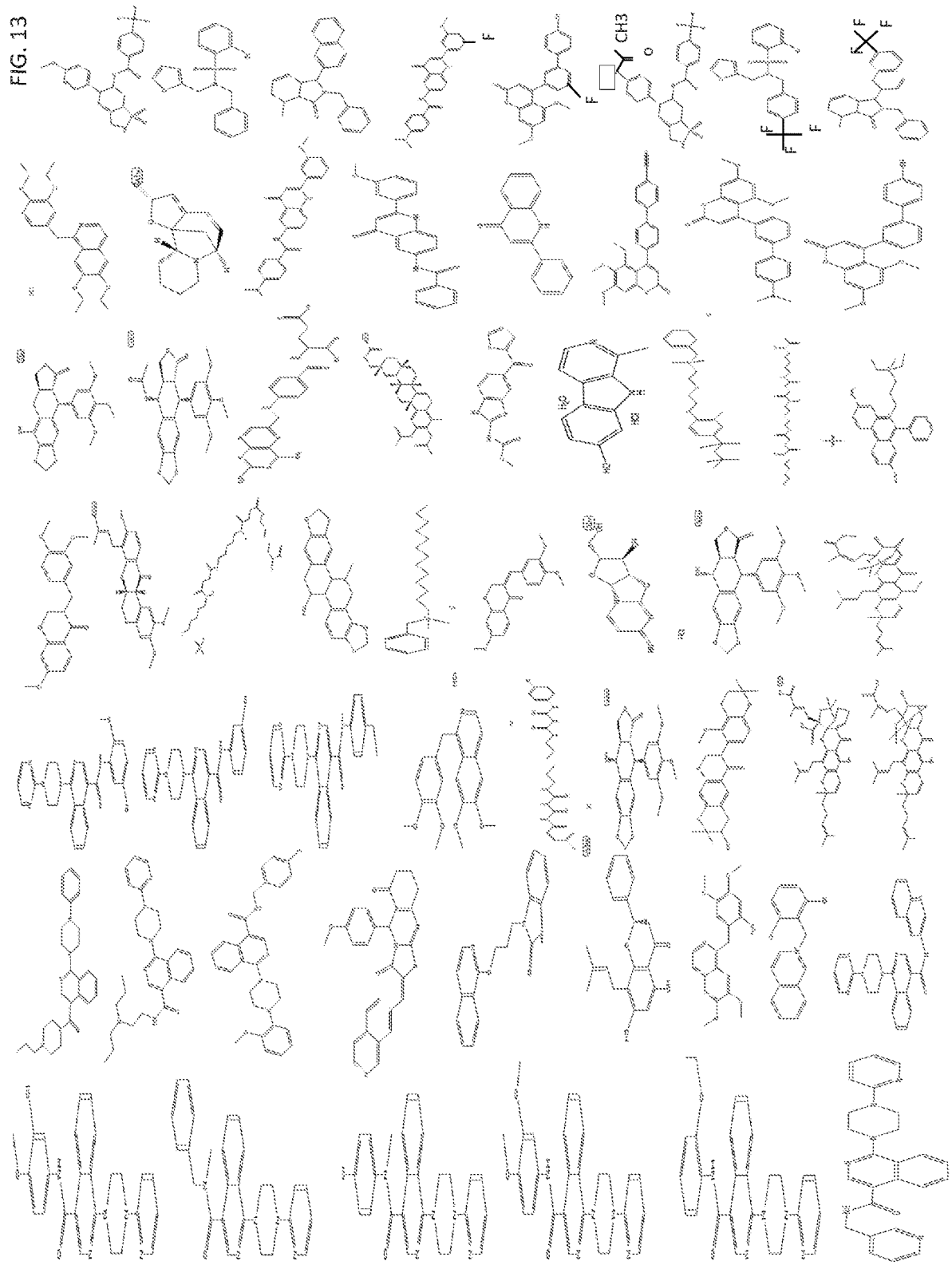

FIG. 8. EN2 is highly expressed in pancreatic cancer, breast cancer, lung cancer and colorectal cancer tissues, but not in their respective normal tissues. (A), Immunohistochemistry (IHC) was performed to measure the expression of EN2 in pancreatic normal and cancer tissues. N=10. (B), IHC was performed to measure the expression of EN2 in breast normal and cancer tissues. N=10. (C), IHC was performed to measure the expression of EN2 in lung normal and cancer tissues. N=10. (D), IHC was performed to measure the expression of EN2 in colorectal normal and cancer tissues. Representative photograph of 10 tissues.

FIG. 9-13. SATB2 and EN2 inhibitor. SATB2 and EN2 inhibitors attenuate transcriptional activity of SATB2 or EN2 at 0.1-15 µM concentrations in breast, prostate, pancreatic and brain cancer stem cells, and cancer cell lines (AsPC-1, PANC-1, PC-3, LNCaP, MCF-7, MDA-MB-231). The $IC_{50}$ for cell viability in breast, prostate, pancreatic and brain CSCs, and cancer cell lines (AsPC-1, PANC-1, PC-3, LNCaP, MCF-7, MDA-MB-231) of these SATB2 or EN2 inhibitors falls between 0.1 to 15 µM. Transcriptinal activity was measured by luciferase assay (Promega). Cell viability was measured by steady glow assay (Promega).

DETAIL DESCRIPTIONS OF THE INVENTION

All illustrations of the drawings are for the purpose of describing selected versions of the present invention and are not intended to limit the scope of the present invention.

Despite significant advances in diagnosis, surgical techniques, development of targeted and adjuvant therapies, metastatic cancer remains at the epicenter of the current clinical challenges limiting the survival of cancer patients. Therefore, a deeper understanding of the metastatic cascade and identification of novel players in the molecular network that could explain differences in the etiology of sporadic cases may serve as a key factor to reduce morbidity and mortality in cancer patients. Efforts aimed at identifying such factors that could be targeted may provide new avenues for cancer detection, prevention and therapeutics.

The involvement of cancer stem cells (CSCs) or progenitor cells in cancer growth and metastasis has recently been realized [1]. CSCs/progenitor cells appear to be the cause of cancer initiation, progression, and metastasis [2-6]. Stem cells heavily depend on the pluripotency maintaining factors (cMyc, Oct-4, Sox-2 and Klf-4) for their self-renewal and survival. Since SATB2 regulates expression of Nanog, cMyc, Oct-4, Sox-2 and Klf-4, it is highly likely that it is capable of inducing cellular transformation/dedifferentiation. Stem cells share many common characteristics with CSCs e.g. expression of cell surface markers and pluripotency maintaining factors. Recent studies demonstrate that residual population of CSCs after surgery or chemotherapy is responsible for cancer relapse.

Cancer stem cells (CSCs), progenitor cells, and tumor initiating cells give rise to tumor bulk through continuous processes of self-renewal and differentiation. CSCs are highly tumorigenic, have a tendency to self-renew, and express certain cell surface markers; for example, pancreatic CSCs express CD133/CD44/CD24/ESA. CSCs are also a cause of tumor relapse, drug resistance, and chemo- and radio-therapy failure. Strategies are being developed towards the targeted destruction of CSCs while sparing the physiological stem cells, which may lead to marked improvement in patient outcome. By altering the expression of genes and pathways by novel agents and approaches, various cancers can be prevented and treated by targeting CSCs and progenitor cells. Selective and targeted elimination of the CSCs may be a key for cancer therapy and prevention.

Pancreatic cancer is one of the leading causes of cancer-related deaths in the Western world, and its incidences are increasing [7]. It is the most deadly disease with a 5-year survival rate of less than 6% [8]. Some of the characteristics of the pancreatic cancer include poor prognosis, late discovery due to silent growth, and resistance to chemotherapy and radiation [9, 10]. Unfortunately, at the time of diagnosis many pancreatic cancers are not resectable due to metastasis to the regional lymph nodes and distant organs, and these characteristics make the management of pancreatic cancer very difficult [11]. Several factors such as genetic, environmental carcinogen, diet and lifestyle may cause pancreatic cancer [10]. Recent studies have demonstrated the contribution of cancer stem cells (CSCs)/tumor initiating cells in tumor initiation, promotion, metastasis and drug resistance. Our recent studies showed the existence of CSCs in pancreatic tissues isolated from human and $Kras^{G12D}$ mice [12-15]. It is believed that the majority of pancreatic cancer originates from pancreatic normal ductal epithelial cells. Although pancreatic cancer stem cells isolated from human primary tumors and $Kras^{G12D}$ mice are tumorigenic, the molecular mechanisms by which human pancreatic normal ductal epithelial (HPNE) cells are transformed to malignant phenotype are not well understood.

In solid tumors, cancer patients die as a result of the metastatic spread of the tumor to the rest of the body. Therefore, there is an urgent need to understand the molecular and cellular basis of metastasis, identifying patients whose tumors are more likely to metastasize, and developing effective therapies against metastatic progression. The epithelial-mesenchymal transition (EMT) is a developmental process that is important for embryogenesis, wound healing, organ fibrosis, and cancer metastasis. Cancer-associated EMT is not a simple process to acquire migration and invasion ability, but a complicated and comprehensive reprogramming, involved in metabolism, epigenetics and differentiation, through which differentiated epithelial cancer cells reverse to an undifferentiated state, not only expressing stem cell markers, but also acquiring stem cell-like functions.

SATB2, a transcription factor and epigenetic regulator [16], regulates gene expression both by modulating chromatin architecture and by functioning as a transcriptional co-factor [17-21]. The SATB2 gene is conserved in humans and mouse. In humans, there are three transcripts which encodes for SATB2 protein. Human and mouse share three Oct-4, one Nanog and two cMyc binding sites on chromosome 2. $SATB2^{-/-}$ mice are defective in bone development and osteoblast differentiation [18]. It is linked to craniofacial patterning and osteoblast differentiation [18], and in development of cortical neurons [19-22]. SATB2 is over expressed in 85% of CRC tumors, suggesting its use as a diagnostic marker for colon cancer [23]. In breast cancer, SATB2 mRNA expression is significantly associated with cancer progression and poor survival [24]. However, the tumor promoting and metastatic roles SATB2 in pancreatic carcinogenesis have never been examined. Stem cells heavily depend on the pluripotency maintaining factors (Nanog, Oct-4, Sox-2 and Klf-4) for their self-renewal and survival. We have demonstrated that pancreatic CSCs expressing CD24, CD44, CD133, and ESA are highly tumorigenic in $NOD/SCID/IL2R\gamma^{null}$ mice [14]. Since SATB2 binding sites are present on Oct-4, Nanog and cMyc, it can directly regulate their expressions and stem cell characteristics. SATB2 may induce malignant transformation and also enhance EMT and metastasis.

Engrailed-2 (EN2) is a transcription factor which belongs to the HOX gene family [25, 26]. It plays a significant role in embryonic development and stem cell self-renewal [25, 26]. Limited studies have described the expression of EN2 in breast, bladder and prostate cancer [25, 27-29], however, the clinical significance of EN2 in breast cancer has not been established. Since the detectable levels of EN2 in the urine of prostate and bladder cancer patients have been detected [28, 30-34], suggesting the use of EN2 as a diagnostic biomarker of cancer. EN2 may also enhance EMT and metastasis.

Suitable cancers which can be treated by inhibiting cancer stem cells using the compositions and methods of the present invention include cancers classified by site or by histological type. Cancers classified by site include cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, nos; ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); cancers of the lymphomas (hodgkin's disease and non-hodgkin's lymphoma), multiple myeloma, and leukemias (lymphocytic leukemia; myeloid leukemia; monocytic leukemia; and other leukemias).

Other cancers, classified by histological type, that may be treated include, but are not limited to, Neoplasm, malignant; Carcinoma, NOS; Carcinoma, undifferentiated, NOS; Giant and spindle cell carcinoma; Small cell carcinoma, NOS;

Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Neuroendocrine tumor; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Branchiolo-alveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Nonencapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extra-mammary paraganglioma, malignant; Pheochromocytoma; Glomangiosarcoma; Malignant melanoma, NOS; Amelanotic melanoma; Superficial spreading melanoma; Malignant melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyo sarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovari, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

In some embodiments, the cancer to be treated and the cancer stem cells to be inhibited are from cancers selected from the group consisting of breast cancer, prostrate cancer, brain cancer, lung cancer, mesothelioma, melanoma, multiple myeloma, colon cancer, kidney cancer, gall bladder cancer, gastrointestinal cancer, ovarian cancer, pancreatic cancer, neuroendocrine tumor, multiple myeloma, leukemia, and lymphoma.

MicroRNAs (miRNAs) are a class of endogenous small non-coding RNAs that have been found highly conserved among species. MicroRNAs are able to negatively regulate gene expression through base pairing of their target genes. MicroRNAs play a significant role in gene regulatory networks through targeting mRNAs. They are involved in diverse biological processes such as cell proliferation, differentiation, stemness, epithelial-mesenchymal transition, inflammation, angiogenesis, tumor growth and metastasis. Due to their pivotal effects on multiple genes and pathways, dysregulated miRNAs have been reported to be associated with different diseases, including cancer and inflammation. During transformation, cells gain the EMT phenotype by inducing transcription factor Zeb1, which inhibits E-cadherin and induces N-cadherin. Cadherin switch occurs during reversal of EMT.

Gene expression levels are determined at the mRNA level (e.g., by RT-PCR, qRT-PCR, QT-PCR oligonucleotide array, etc) or at the protein level (e.g., by Western blot, ELISA, antibody microarray, etc.). Preferred methodologies for determining mRNA expression levels include quantitative reverse transcriptase PCR (QT-PCR), quantitative real-time RT-PCR, oligonucleotide microarray, transcriptome array, microRNA array, gene chip array, methylation array, or combination thereof. Preferred methodologies for determining protein expression levels include the use of ELISAs, Western blotting, and antibody microarrays. The ratios of gene expression and protein expression can also be used.

One aspect of the present application relates to methods for treating cancer condition in a subject. In certain embodiments, the method comprises administering to the subject an effective amount of a first agent that inhibits Engrailed-2 (EN2) expression and/or EN2 activity and administering to the subject an effective amount of a second agent that inhibits SATB2 expression and/or SATB2 activity.

In other embodiments, the expression of genes and proteins will be determined in the body fluid, serum, blood, plasma, urine, exosomes and tissue samples.

In other embodiments, EN2 and SATB2 activities are defined as their transcriptional activities or protein activities. Inhibitors of EN2 and/or SATB2 by small organic molecules, shRNA, siRNA, microRNA, or natural products will inhibit their transcriptional activities and expression, and also EN2- or SATB2-dependent gene transcription. EN2 and/or SATB2 inhibitors will inhibit growth of cancer stem cells, progenitor cells, cancer cells, angiogenesis, inflammation, epithelial mesenchymal transition, malignant transformation, cancer growth and metastasis.

In other embodiments, the method further comprises determining the expression of estrogen receptor, progesterone receptor, androgen receptor, Her2/neu, Bcr-Abl, Pdx-1, Kras, cMyc, MAP kinase status etc in cells, tissues or bodily fluids obtained from the cancer patients. The status of these genes and proteins may be used, in combination with the inhibitors of EN2 and/or SATB2 for determining the cancer conditions and treatment in the subject.

Synthetically produced siRNAs may incorporate any chemical modifications to the RNA structure that are known to enhance siRNA stability and functionality. In some cases, the siRNAs may be synthesized as a locked nucleic acid (LNA)-modified siRNA.

In certain embodiments, the siRNA or shRNA and the corresponding EN2 or SATB2 cDNA sequences are published in the literature and internet, and can be obtained from the gene bank.

Alternatively, or in addition, EN2 siRNA comprising a synthetic EN2-directed siRNA may be used to silence or reduce EN2 expression in cancer cells.

Alternatively, or in addition, SATB2 siRNA comprising a synthetic SATB2-directed siRNA may be used to silence or reduce SATB2 expression in cancer cells.

Synthetic siRNAs and shRNAs may be designed using well known algorithms and synthesized using a conventional DNA/RNA synthesizer. SATB2 and EN2 siRNAs, as well as SATB2 and EN2 shRNA expression constructs may be commercially obtained.

An aptamer-siRNA chimera is a targeted siRNA comprising an siRNA chemically linked to a cell internalizing aptamer. An aptamer is a nucleic acid version of an antibody that comprises a class of oligonucleotides that can form specific three dimensional structures exhibiting high affinity binding to a wide variety of cell surface molecules, proteins, and/or macromolecular structures. Typically, aptamers are small nucleic acids ranging from 15-50 bases in length that fold into defined secondary and tertiary structures, such as stem-loops or G-quartets. Aptamers can bind small molecules, such as ATP and theophylline, as well as large molecules, such as reverse transcriptase, thrombin, and a variety of cell surface receptors.

An aptamer can be chemically linked or conjugated to the above described nucleic acid inhibitors to form targeted nucleic acid inhibitors (Ray et al., Pharmaceuticals, 3:1761-1778, 2010). An aptamer-siRNA chimera contains a targeting moiety in the form of an aptamer which is linked to an siRNA. In one embodiment, the inhibitor comprises a chimeric aptamer-si RNA oligonucleotide capable of targeting cancer tissues. Preferably, the aptamer is a cell internalizing aptamer. Upon binding to specific cell surface molecules, the aptamer can facilitate internalization into the cell where the nucleic acid inhibitor acts. In one embodiment both the aptamer and the siRNA comprises RNA. The aptamer and the siRNA may comprise any nucleotide modifications as further described herein. In a specific embodiment, the aptamer comprises a targeting moiety such as binding the prostate-specific membrane antigen (PSMA) or mesothelin.

Aptamers can bind very tightly with Kds from the target molecule of less than 10-12 M. Aptamers can bind the target molecule with a very high degree of specificity. For example, aptamers have been isolated that have greater than a 10,000 fold difference in binding affinities between the target molecule and another molecule that differ at only a single position on the molecule.

In another embodiment, one or both of the first and second bioactive components may comprise an antisense oligonucleotide or polynucleotide. The antisense oligonucleotide or polynucleotide may comprise a DNA backbone, RNA backbone, or chemical derivative thereof. In one embodiment, one or both of the first and second bioactive components comprises a single stranded antisense oligonucleotide or polynucleotide targeting EN2 and/or SATB2 for degradation. In preferred embodiments, the bioactive component comprises a single stranded antisense oligonucleotide complementary to EN2 and/or SATB2 mRNA sequences. The single stranded antisense oligonucleotide or polynucleotide may be synthetically produced or it may be expressed from a suitable expression vector. The antisense nucleic acid is designed to bind via complementary binding to the mRNA sense strand so as to promote RNase H activity, which leads to degradation of the mRNA. Preferably, the antisense oligonucleotide is chemically or structurally modified to promote nuclease stability and/or increased binding.

In some embodiments, the antisense oligonucleotides are modified to produce oligonucleotides with nonconventional chemical or backbone additions or substitutions, including but not limited to peptide nucleic acids (PNAs), locked nucleic acids (LNAs), morpholino backboned nucleic acids, methylphosphonates, duplex stabilizing stilbene or pyrenyl caps, phosphorothioates, phosphoroamidates, phosphotriesters, and the like. By way of example, the modified oligonucleotides may incorporate or substitute one or more of the naturally occurring nucleotides with an analog; internucleotide modifications incorporating, for example, uncharged linkages (e.g., methyl phosphonates, phosphotriesters, phosphoamidates, carbamates, etc.) or charged linkages (e.g., phosphorothioates, phosphorodithioates, etc.); modifications incorporating intercalators (e.g., acridine, psoralen, etc.), chelators (e.g., metals, radioactive metals, boron, oxidative metals, etc.), or alkylators, and/or modified linkages (e.g., alpha anomeric nucleic acids, etc.).

In some embodiments, the single stranded oligonucleotides are internally modified to include at least one neutral charge in its backbone. For example, the oligonucleotide may include a methylphosphonate backbone or peptide nucleic acid (PNA) complementary to the target-specific sequence. These modifications have been found to prevent or reduce helicase-mediated unwinding. The use of uncharged probes may further increase the rate of hybridization to polynucleotide targets in a sample by alleviating the repulsion of negatively-charges nucleic acid strands in classical hybridization (Nielsen et al., 1999, Curr. Issues Mol. Biol., 1:89-104). PNA oligonucleotides are uncharged nucleic acid analogs for which the phosphodiester backbone has been replaced by a polyamide, which makes PNAs a polymer of 2-aminoethyl-glycine units bound together by an amide linkage. PNAs are synthesized using the same Boc or Fmoc chemistry as are use in standard peptide synthesis. Bases (adenine, guanine, cytosine and thymine) are linked to the backbone by a methylene carboxyl linkage. Thus, PNAs are acyclic, achiral, and neutral. Other properties of PNAs are increased specificity and melting temperature as compared to nucleic acids, capacity to form triple helices, stability at acid pH, non-recognition by cellular enzymes like nucleases, polymerases, etc. (Rey et al., 2000, FASEB J., 14:1041-1060; Nielsen et al., 1999, Curr. Issues Mol. Biol., 1:89-104).

Methylphosphonate-containing oligonucleotides are neutral DNA analogs containing a methyl group in place of one of the non-bonding phosphoryl oxygens. Oligonucleotides with methylphosphonate linkages were among the first reported to inhibit protein synthesis via anti-sense blockade of translation. However, the synthetic process yields chiral molecules that must be separated to yield chirally pure monomers for custom production of oligonucleotides (Reynolds et al., 1996, Nucleic Acids Res., 24:4584-4591).

In some embodiments, the phosphate backbone in the oligonucleotides may contain phosphorothioate linkages or phosphoroamidates. Combinations of such oligonucleotide linkages are also within the scope of the present invention.

In other embodiments, the oligonucleotide may contain a backbone of modified sugars joined by phosphodiester internucleotide linkages. The modified sugars may include furanose analogs, including but not limited to 2-deoxyribofuranosides, .alpha.-D-arabinofuranosides, .alpha.-2'-deoxyribofuranosides, and 2',3'-dideoxy-3'-aminoribofuranosides. In alternative embodiments, the 2-deoxy-.beta.-D-ribofuranose groups may be replaced with other sugars, for example, .beta.-D-ribofuranose. In addition, .beta.-D-ribofuranose may be present wherein the 2-OH of the ribose moiety is alkylated with a C1-6 alkyl group (2-(O—C1-6 alkyl) ribose) or with a C2-6 alkenyl group (2-(O—C2-6 alkenyl) ribose), or is replaced by a fluoro group (2-fluororibose). Related oligomer-forming sugars include those used in locked nucleic acids (LNA).

Chemically modified oligonucleotides may also include, singly or in any combination, 2'-position sugar modifications, 5-position pyrimidine modifications (e.g, 5-(N-benzylcarboxyamide)-2'-deoxyuridine, 5-(N-isobutylcarboxyamide)-2'-deoxyuridine, 5-(N-[2-(1H-indole-3yl)ethyl]carboxyamide)-2'-deoxyuridine, 5-(N-[1-(3-trimethylammonium)propyl]carboxyamide)-2'-deoxyuridine chloride, 5-(N-napthylcarboxyamide)-2'-deoxyuridine, and 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, methylations, unusual base-pairing combinations, such as the isobases isocytidine and isoguanidine, and the like.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming oligonucleotides (TFOs) are molecules that can interact with either double-stranded and/or single-stranded nucleic acid. TFOs can bind target regions with high affinity and specificity. In preferred embodiments, the triplex forming molecules bind the target molecule with a Kd less than 10-6, 10-8, 10-10, or 10-12. Exemplary TFOs for use in the present invention include PNAs, LNAs, and LNA modified PNAs, such as Zorro-LNAs (Ge et al., FASEB J., 21:1902-1914, 2007; Zaghloul et al., Nucl. Acids Res., 39(3):1142-1154, 2011).

In one embodiment, the agent that inhibits EN2 expression and/or EN2 activity comprises one or more members selected from the group consisting of EN2 siRNA, aptamer-siRNA chimera, single stranded antisense oligonucleotide, triplex forming oligonucleotide, ribozyme, external guide sequence, polynucleotide encoding a EN2 siRNA.

In one embodiment, the agent that inhibits SATB2 expression and/or SATB2 activity comprises one or more members selected from the group consisting of SATB2 siRNA, aptamer-siRNA chimera, single stranded antisense oligonucleotide, triplex forming oligonucleotide, ribozyme, external guide sequence, polynucleotide encoding a SATB2 siRNA.

In another embodiment, a method for treating a cancer condition in a subject, comprises: (a) determining expression levels of EN2, and/or SATB2, (b) based on the results of (a), (1) administering to the subject an effective amounts of an agent that inhibits EN2 expression and (2) an agent that inhibits SATB2 expression and/or SATB2 activity.

In certain embodiments, the method for monitoring or diagnosing cancerous, pre-cancerous, and non-cancerous conditions in a test subject comprises determining EN2 and/or SATB2 expression level in cells or bodily fluids obtained from the test subject suspected to be at risk for cancer, determining an EN2 expression level in cells or bodily fluids obtained from the test subject suspected to be at risk for cancer, and comparing the EN2 and SATB2 expression levels from the tissue of the test subject with the expression levels obtained from the same tissue of a cancer-free control subject, wherein expression level increases of at least 2-fold in each of EN2 and SATB2 in the test subject relative to the control subject are indicative of cancer or of an increased risk for developing cancer. Expression level increases of at least 20% or more may be observed. The cells may be obtained from any tissue in which EN2 and/or SATB2 are upregulated in cancer. Preferred tissues include, but not limited to, breast, colon, brain, pancreas, stomach, ovary, prostate and blood tissue. Preferred bodily fluids include blood, plasma, serum, and urine.

In certain embodiments, the method may alternatively or additionally comprise the step of determining EN2, and/or SATB2 expression level in the cells or bodily fluids obtained from the test subject, and comparing those expression levels to corresponding reference levels (e.g., expression levels obtained from the cells or bodily fluids of normal control subjects), wherein expression levels of EN2 and/or SATB2 in the test subject relative to the control are indicative of cancer or a risk for developing cancer.

In addition, the herein disclosed methods can comprise the detection, including measurement, of EN2, and/or SATB2 in bodily fluids of the subject, such as blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

Gene expression levels and gene expression ratios may be determined at the mRNA level (e.g., by RT-PCR, QT-PCR, oligonucleotide array, etc) or at the protein level (e.g., by Western blot, antibody microarray, ELISA, etc.). Preferred methodologies for determining mRNA expression levels (and ratios therefrom) include quantitative reverse transcriptase PCR (QT-PCR), quantitative real-time RT-PCR, oligonucleotide microarray, antibody microarray, or combination thereof. Preferred methodologies for determining protein expression levels (and ratios therefrom) include the use of ELISAs and antibody microarrays.

In some embodiments, the method further comprises determining the expression of, but not limited to, androgen receptor (AR), estrogen receptor, Kras, Bcr-Abl, cMyc, Nanog, Oct-4, Sox-2, KLF4 status in cancer cells or bodily fluids obtained from the test subject. The status of these genes and/or proteins can be used for determining the cancer conditions in the subject.

The monitoring and diagnosing methods of the present invention provide clinicians with a prognostic indicator for initiated or pre-cancerous tissue. Candidates for this test include patients at high risk (based on age, race) for cancer. As a diagnostic, positive or negative EN2 and/or SATB2 tests can then be followed by additional screening with biomarkers to determine cancer status. In addition, these patients can be candidates for treatment with EN2 and/or SATB2 regulators. Alternatively, these tests can be used on patients to monitor the effectiveness of their cancer therapy, to determine treatment course, or to monitor cancer recurrence.

Identification of blood protein markers can provide a more accurate or earlier diagnosis of cancer can have a positive impact on cancer treatment and management. As disclosed herein, aberrant EN2 and/or SATB2 expression occurs early in the progression of cancer and can be an initiating event in tumorigenesis. Therefore, samples from patients collected to screen for the presence of EN2 and SATB2 mRNA and/or protein or antigens can be used for the early detection of cancer.

In a further aspect, the present invention provides compositions for treating cancer in accordance with the methods described herein. In one embodiment, the composition comprises a first agent that inhibits EN2 expression and/or EN2 activity, a second agent that inhibits SATB2 expression and/or SATB2 activity, and a pharmaceutically acceptable carrier. The composition may further include a third agent that modulates expression and/or activity of EN2 and SATB2.

Small Organic Molecules

In certain embodiments, EN2 and/or SATB2 activity and/or expression will be inhibited by small organic molecules. Small organic molecules have been successfully used to inhibit activities of several transcriptional factors which ultimately modulate tumor growth and metastasis. Similarly, small organic molecule inhibitors of EN2 and/or SATB2 will inhibit stemness, epithelial mesenchymal transition, malignant transformation, cancer growth, angiogenesis and metastasis.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an," when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "amino" means —$NH_2$; the term "nitro" means —$NO_2$; the term "halo" designates —F, —Cl, —Br or —I; the term "mercapto" means —SH; the term "cyano" means —CN; the term "silyl" means —$SiH_3$, and the term "hydroxy" means —OH.

The term "heteroatom-substituted," when used to modify a class of organic radicals (e.g. alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, =O, =S, —$NO_2$, —$N(CH_3)_2$, amino, or —SH. Specific heteroatom-substituted organic radicals are defined more fully below.

The term "heteroatom-unsubstituted," when used to modify a class of organic radicals (e.g., alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group —$C_6H_4C\equiv CH$ is an example of a heteroatom-unsubstituted aryl group, while —$C_6H_4F$ is an example of a heteroatom-substituted aryl group. Specific heteroatom-unsubstituted organic radicals are defined more fully below.

The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The term "alkyl" includes straight-chain alkyl groups, branched-chain alkyl groups, cycloalkyl (alicyclic) groups, alkyl heteroatom-substituted cycloalkyl groups, and cycloalkyl heteroatom-substituted alkyl groups. The groups, —$CH_3$, —$CH_2CH_3$, —$CH_2CH_2CH_3$, —$CH(CH_3)_2$, —$CH(CH_2)_2$, —$CH_2CH_2CH_2CH_3$, —$CH(CH_3)CH_2CH_3$, —$CH_2CH(CH_3)_2$, —$C(CH_3)_3$, —$CH_2C(CH_3)_3$, cyclopentyl, and cyclohexyl, are all examples of heteroatom-unsubstituted alkyl groups.

The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH(CH_2)_2$, —$CH_2OCH_2CF_3$, —$CH_2OCOCH_3$, —$CH_2NH_2$, —$CH_2NHCH_3$, —$CH_2N$ $(CH_3)_2$, —$CH_2NHCH_2CH_3$, —$CH_2N(CH_3)CH_2CH_3$, —$CH_2NHCH_2CH_2CH_3$, —$CH_2NHCH(CH_3)_2$, —$CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2I$, —$CH_2CH_2OH$, $CH_2CH_2OCOCH_3$, —$CH_2CH_2NH_2$, —$CH_2CH_2N(CH_3)_2$, —$CH_2CH_2NHCH_3$, —$CH_2CH_2N(CH_3)CH_2CH_3$, —$CH_2CH_2NHCH_2CH_2CH_3$, —$CH_2CH_2NHCH(CH_3)_2$, —$CH_2CH_2NHCH(CH_2)_2$, —$CH_2CH_2N(CH_2CH_3)_2$, —$CH_2CH_2NHCO_2C(CH_3)_3$, and —$CH_2Si(CH_3)_3$.

The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —$CH=CH_2$, —$CH=CHCH_3$, —$CH=CHCH_2CH_3$, —$CH=CHCH_2CH_2CH_3$, —$CH=CHCH(CH_3)_2$, —$CH=CHCH(CH_2)_2$, —$CH_2CH=CH_2$, —$CH_2CH=CHCH_3$, —$CH_2CH=CHCH_2CH_3$, —$CH_2CH=CHCH_2CH_2CH_3$, —$CH_2CH=CHCH(CH_3)_2$, —$CH_2CH=CHCH(CH_2)_2$, and —$CH=CH$—$C_6H_5$.

The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —$CH=CHF$, —$CH=CHCl$ and —$CH=CHBr$, are examples of heteroatom-substituted alkenyl groups.

The term "heteroatom-unsubstituted $C_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —$C\equiv CH$, —$C\equiv CCH_3$, and —$C\equiv CC_6H_5$ are examples of heteroatom-unsubstituted alkynyl groups.

The term "heteroatom-substituted $C_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —$C\equiv CSi(CH_3)_3$, is an example of a heteroatom-substituted alkynyl group.

The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Examples of heteroatom-unsubstituted aryl groups include phenyl, methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, $C_6H_4CH=CH_2$, —$C_6H_4CH=CHCH_3$, —$C_6H_4C\equiv CH$, —$C_6H_4C\equiv CCH_3$, naphthyl, quinolyl, indolyl, and the radical derived from biphenyl. The term "heteroatom-unsubstituted aryl" includes carbocyclic aryl groups, biaryl groups, and radicals derived from polycyclic fused hydrocarbons (PAHs).

The term "heteroatom-substituted $C_n$-aryl" refers to a radical, refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. The term "heteroatom-substituted aryl" includes heteroaryl and heterocyclic aryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OCOCH_3$, —$C_6H_4OC_6H_5$, —$C_6H_4NH_2$, —$C_6H_4NHCH_3$, —$C_6H_4NHCH_2CH_3$, —$C_6H_4CH_2Cl$, —$C_6H_4CH_2Br$, —$C_6H_4CH_2OH$, —$C_6H_4CH_2OCOCH_3$, —$C_6H_4CH_2NH_2$, —$C_6H_4N(CH_3)_2$, —$C_6H_4CH_2CH_2Cl$, —$C_6H_4CH_2CH_2OH$, —$C_6H_4CH_2CH_2OCOCH_3$, —$C_6H_4CH_2CH_2NH_2$, —$C_6H_4CH_2CH=CH_2$, —$C_6H_4CF_3$, —$C_6H_4CN$, —$C_6H_4C\equiv CSi(CH_3)_3$, —$C_6H_4COH$, —$C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, and imidazoyl.

The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. An "aralkyl" includes an alkyl heteroatom-substituted with an aryl group. Examples of heteroatom-unsubstituted aralkyls include phenylmethyl (benzyl) and phenylethyl.

The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —$COCH_3$, —$COCH_2CH_3$, —$COCH_2CH_2CH_3$, —$COCH(CH_3)_2$, —$COCH(CH_2)_2$, —$COC_6H_5$, —$COC_6H_4CH_3$, —$COC_6H_4CH_2CH_3$, —$COC_6H_4CH_2CH_2CH_3$, —$COC_6H_4CH(CH_3)_2$, —$COC_6H_4CH(CH_2)_2$, and —$COC_6H_3(CH_3)_2$, are examples of heteroatom-unsubstituted acyl groups.

The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —$COCH_2CF_3$, —$CO_2H$, $CO_2CH_3$, —$CO_2CH_2CH_3$, —$CO_2CH_2CH_2CH_3$, —$CO_2CH(CH_3)_2$, —$CO_2CH(CH_2)_2$, —$CONH_2$, —$CONHCH_3$, —$CONHCH_2CH_3$, —$CONHCH_2CH_2CH_3$, —$CONHCH(CH_3)_2$, —$CONHCH(CH_2)_2$, —$CON(CH_3)_2$, —$CON(CH_2CH_3)CH_3$, —$CON(CH_2CH_3)_2$ and —$CONHCH_2CF_3$, are examples heteroatom-substituted acyl groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —$OCH_3$, —$OCH_2CH_3$, —$OCH_2CH_2CH_3$, —$OCH(CH_3)_2$, and —$OCH(CH_2)_2$.

The term "heteroatom-substituted $C_n$-alkoxy" refers to a group, having the structure —OR, in which R is a heteroatom-substituted $C_n$-alkyl, as that term is defined above. For example, —$OCH_2CF_3$ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above.

The term "heteroatom-substituted $C_n$-alkenyloxy" refers to a group, having the structure —OR, in which R is a heteroatom-substituted $C_n$-alkenyl, as that term is defined above.

The term "heteroatom-unsubstituted $C_n$-alkynyloxy" refers to a group, having the structure —OR, in which R is a heteroatom-unsubstituted $C_n$-alkynyl, as that term is defined above.

The term "heteroatom-substituted $C_n$-alkynyloxy" refers to a group, having the structure —OR, in which R is a heteroatom-substituted $C_n$-alkynyl, as that term is defined above.

The term "heteroatom-unsubstituted $C_n$-aryloxy" refers to a group, having the structure —OAr, in which Ar is a heteroatom-unsubstituted $C_n$-aryl, as that term is defined above. An example of a heteroatom-unsubstituted aryloxy group is —$OC_6H_5$.

The term "heteroatom-substituted $C_n$-aryloxy" refers to a group, having the structure —OAr, in which Ar is a heteroatom-substituted $C_n$-aryl, as that term is defined above.

The term "heteroatom-unsubstituted $C_n$-aralkyloxy" refers to a group, having the structure —OAr, in which Ar is a heteroatom-unsubstituted $C_n$-aralkyl, as that term is defined above.

The term "heteroatom-substituted $C_n$-aralkyloxy" refers to a group, having the structure —OAr, in which Ar is a heteroatom-substituted $C_n$-aralkyl, as that term is defined above.

The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —$OCOCH_3$ is an example of a heteroatom-unsubstituted acyloxy group.

The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —$NHCH_3$, —$NHCH_2CH_3$, —$NHCH_2CH_2CH_3$, —$NHCH(CH_3)_2$, —$NHCH(CH_2)_2$, —$NHCH_2CH_2CH_2CH_3$, —$NHCH(CH_3)CH_2CH_3$, —$NHCH_2CH(CH_3)_2$, —$NHC(CH_3)_3$, —$N(CH_3)_2$, —$N(CH_3)CH_2CH_3$, —$N(CH_2CH_3)_2$, N-pyrrolidinyl, and N-piperidinyl.

The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted $C_n$-alkenylamino groups also include dialkenylamino and alkyl(alkenyl)amino groups.

The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl(alkynyl)amino groups.

The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups.

The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups.

The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above. The term "heteroatom-substituted aralkylamino" includes the term "heteroaralkylamino."

The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The term amido includes N-alkyl-amido, N-aryl-amido, N-aralkyl-amido, acylamino, alkylcarbonylamino, arylcarbonylamino, and ureido groups. The group, —NHCOCH$_3$, is an example of a heteroatom-unsubstituted amido group.

The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group. The term "heteroatom-substituted $C_n$-alkylthio" refers to a group, having the structure —SR, in which R is a heteroatom-substituted $C_n$-alkyl, as that term is defined above.

The term "heteroatom-unsubstituted $C_n$-alkenylthio" refers to a group, having the structure —SR, in which R is a heteroatom-unsubstituted $C_n$-alkenyl, as that term is defined above.

The term "heteroatom-substituted $C_n$-alkenylthio" refers to a group, having the structure —SR, in which R is a heteroatom-substituted $C_n$-alkenyl, as that term is defined above.

The term "heteroatom-unsubstituted $C_n$-alkynylthio" refers to a group, having the structure —SR, in which R is a heteroatom-unsubstituted $C_n$-alkynyl, as that term is defined above.

The term "heteroatom-substituted $C_n$-alkynylthio" refers to a group, having the structure —SR, in which R is a heteroatom-substituted $C_n$-alkynyl, as that term is defined above.

The term "heteroatom-unsubstituted $C_n$-arylthio" refers to a group, having the structure —SAr, in which Ar is a heteroatom-unsubstituted $C_n$-aryl, as that term is defined above. The group, —$SC_6H_5$, is an example of a heteroatom-unsubstituted arylthio group.

The term "heteroatom-substituted $C_n$-arylthio" refers to a group, having the structure —SAr, in which Ar is a heteroatom-substituted $C_n$-aryl, as that term is defined above.

The term "heteroatom-unsubstituted $C_n$-aralkylthio" refers to a group, having the structure —SAr, in which Ar is a heteroatom-unsubstituted $C_n$-aralkyl, as that term is defined above. The group, —$SCH_2C_6H_5$, is an example of a heteroatom-unsubstituted aralkyl group.

The term "heteroatom-substituted $C_n$-aralkylthio" refers to a group, having the structure —SAr, in which Ar is a heteroatom-substituted $C_n$-aralkyl, as that term is defined above.

The term "heteroatom-unsubstituted $C_n$-acylthio" refers to a group, having the structure —SAc, in which Ac is a heteroatom-unsubstituted $C_n$-acyl, as that term is defined above. The group, —$SCOCH_3$, is an example of a heteroatom-unsubstituted acylthio group.

The term "heteroatom-substituted $C_n$-acylthio" refers to a group, having the structure —SAc, in which Ac is a heteroatom-substituted $C_n$-acyl, as that term is defined above. The term "heteroatom-unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted $C_1$-$C_{10}$-alkylsilyl has 1 to 10 carbon atoms. An alkylsilyl group includes dialkylamino groups. The groups, —$Si(CH_3)_3$ and —$Si(CH_3)_2C(CH_3)_3$, are examples of heteroatom-unsubstituted alkylsilyl groups.

The term "heteroatom-substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like.

Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts are known to one of ordinary skill in the art.

SATB2 and/or EN2 inhibitors also include the modifications by any functional groups such as aromatic rings, alkyl chains, alkenes, alkynes, ester, ether, alicyclic rings, halogens, ketone, fluorine, oxygen, chlorine, bromine, iodine, astatine, nitrogen, carbamate, thiol, hydroxyl, theol, amide, amines, carboxylic acid, trifluoromethyl, hydroxyl, sulfonamide, aldehyde, nitrile, nitro, thiol, and methoxy.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "$IC_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

Synthetically produced small organic molecules may incorporate any chemical modifications to the structure that are known to enhance solubility, stability, binding to target, bioavailability and functionality.

Small organic molecule inhibitors of EN2 and/or SATB2 will be delivered in nanoparticles (synthetic or biological materials) conjugated with or without targeting agents. Small organic molecule inhibitors of EN2 and/or SATB2 may be delivered using silver nanoparticles, gold nanoparticles, liposomes, micelles, dendrimers, polymers, cellulose, esters, biodegradable particles, and artificial DNA nanostructure.

Small organic molecule inhibitors of EN2 and/or SATB2 can be combined with other chemotherapeutic drugs and/or irradiation for the treatment and prevention of cancer.

Inhibition of EN2 and/or SATB2 Expression and/or Activity by Natural Products

Natural molecules from natural sources including plants, microbes and marine organisms have been the basis of treatment of human diseases since the ancient times. Compounds derived from nature have been important sources of new drugs and also serve as templates for synthetic modification. Many successful anti-cancer drugs currently in use are naturally derived or their analogues and many more are under clinical trials. Natural products have been a rich source of compounds for drug discovery. Natural products are generally non-toxic to humans.

In certain embodiments, EN2 and/or SATB2 activity and/or expression will be inhibited by plant derived chemicals. These plant derived chemicals may comprised of pure chemical/compound or a mixture of chemicals. Natural products have successfully been used to inhibit cancer cell proliferation, tumor growth, angiogenesis and metastasis. Similarly, natural products either pure or complex, will inhibit EN2 and/or SATB2 activity and/or expression in cancer cells. Natural product inhibitors of EN2 and/or SATB2 will inhibit stemness, epithelial mesenchymal transition, malignant transformation, angiogenesis, cancer growth and metastasis.

Natural products either isolated from plants or synthetically produced may incorporate any chemical modifications to the structure that are known to enhance solubility, stability, binding to target, bioavailability and functionality.

Natural product inhibitors of EN2 and/or SATB2 will be delivered in nanoparticles (synthetic or biological materials) conjugated with or without targeting agents. Natural product inhibitors of EN2 and/or SATB2 can be delivered using silver nanoparticles, gold nanoparticles, liposomes, micelles, dendrimers, polymers, cellulose, esters, biodegradable particles, and artificial DNA nanostructure.

Natural product inhibitors of EN2 and/or SATB2 can be combined with other chemotherapeutic drugs and/or irradiation for the treatment and prevention of cancer.

Administration of EN2 and/or SATB2 Inhibitors

The compounds of the present invention may be administered, e.g., orally or by injection (e.g. subcutaneous, intravenous, intraperitoneal, etc.) Depending on the route of administration, the active compound may be coated in a material to protect the compound from the action of acids and other natural conditions which may inactivate the compound. In the case of cancer therapy, the agents may be administered intra-tumorally, circumferential to a tumor mass, locally to the tumor vasculature or lymphatic system, regionally or systemically. They may also be administered to a resected tumor bed, for example, by syringing or by a post-operative catheter with continuous perfusion/infusion.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

Compounds of the invention may also be formulated for local administration, e.g., for topical administration to the skin or mucosa, for topical administration to the eye, for delivery to the lungs by inhalation, or by incorporation into a biocompatible matrix for controlled release to a specified site over an extended period of time (e.g., as an active ingredient in a drug-eluting cardiac stent). In certain cases significant systemic concentrations may also be achieved by these routes of administration (e.g., via pulmonary or transmucosal delivery).

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials may be in solution, suspension (for example, incorporated into microparticles, liposomes, or cells). These may be targeted to a particular cell type via antibodies, receptors, or receptor ligands. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

The compositions described herein can be packaged together in any suitable combination as a kit useful for performing, or aiding in the performance of, the disclosed method. In some embodiments, the kit for treating cancer conditions, comprises an inhibitor of EN2 expression or activity, an inhibitor of SATB2 expression or activity. The inhibitors or activators may comprise any of the described bioactive components.

A composition disclosed herein may be administered in a number of ways depending on whether local or systemic treatment is desired, and on the area to be treated. For example, the compositions may be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

The exact amount of the compositions required will vary from subject to subject, depending on the species, age, weight and general condition of the subject, the particular nucleic acid or vector used, its mode of administration and the like. Guidance can be found in the literature for appropriate dosages for given classes of pharmaceutical products. For example, a typical daily dosage of the disclosed composition used alone might range from about 1 µg/kg to up to 100 mg/kg of body weight or more per day, depending on the factors mentioned above. The monitoring EN2 and/or SATB2 expression levels can be used to predict drug response or resistance, as well as identify patients who may be candidates for anti-EN2, and/or anti-SATB2 therapy. The terms "anti-EN2 therapy" and "anti-SATB2 therapy" refers to methods for inhibiting EN2/SATB2 expression or EN2/SATB2 activity.

In some embodiments, the agents described herein are combined with one or more conventional chemotherapeutic agents. Exemplary chemotherapeutic agents for use in the present invention include 5-alpha-reductase inhibitors, including finasteride, dutasteride, turosteride, bexlosteride, izonsteride, FCE 28260, and SKF 105, 111; integrin-linked kinase (ILK) inhibitors, such as QLT-0267; secreted frizzled-related protein-1 (sFRP1), secreted frizzled-related protein-2 (sFRP2), secreted frizzled related protein-3 (sFRP3/1-RZB), secreted frizzled-related protein-4 (sFRP4), secreted frizzled-related protein-5 (SFRPS), Dickkopf-1 (DKK1), Dickkopf-2 (DKK2), Dickkopf-3 (DKK3), Wnt inhibitory factor-1 (WIF1), cerberus, sclerostin, IWR-1-endo, IWP-2, IWP-3, IWP4, pyrvinium, XAV939, and other WNT signalling pathway inhibitors; bevacizumab (Avastin), cabazitaxel, ketoconazole, prednisone, Sipuleucel-T (APC8015, Provenge), Alpharadin (radium-223 chloride), MDV3100, orteronel (TAK-700), PROSTVAC, cabozantinib (XL-184), DMAPT; cyclopamine, vismodegib, and other hedgehog (Hh) signalling pathway inhibitors; flutamide, luprolide, antiestrogens, such as tamoxifen; antimetabolites and cytotoxic agents, such as daunorubicin, flourouracil, floxuridine, interferon alpha, methotrexate, plicamycin, mecaptopurine, thioguanine, adramycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, idamycin, hormones such as, medroxyprogesterone, estramustine, ethinyl oestradiol, oestradiol, leuprolide, megestrol, octreotide, diethylstilbestrol, chlorotrianisene, etoposide, podophyllotoxin, goserelin, nitrogen mustard derivatives such as, melphalan, chlorambucil, methlorethamine, thiotepa, steroids such as, betamethasone, and other antineoplastic agents such as live Mycobacterium bovis, dicarbazine, asparaginase, leucovoribn, mitotane, vincristine, vinblastine, texotere, cydophosphamide, adriamycin, 5-flourouracil, hexamethylmelamine, acivicin; aclarubicin; acodazole hydrochloride; acrqnine; adozolesin; aldesloukin; altretamine; ambomycin; ametantrone acetate; aminogluthimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomyrin; edatrexate; eflomithine hydrochloride; elsamitrucin; enloplatin; enprorfate; epipropidine; epirubicin hydrochloride; erbulozole; esorubicin hydrochloride; estramustine; estramustine phosphate sodium; etanidazole; ethiodized oil I 131; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; gold Au 198; hydroxyurea; idarubicin hydrochloride; ifosfamide; ilmofosine; interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; strontium chloride Sr 89; sulofenur; talisomycin; taxane; taxoid; tecogalan sodium; tegafur; teloxantrone hydrochloride; temoporfin; teniposide; teroxirono; testolactone; thiamiprine; thioguanine; thiotepa; tiazofurin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, 20-epi-1,25 dihydroxyvitamin D3; 5-ethynyluracil; abiraterone, aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; DHEA; bromineepiandrosterone; epiandrosterone; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTSA; arginine deaminase; asulacrine; atamestane; atrimustine; axinastatin 1; axinastatin 2; axinastatin 3; azasetron; azatoxin; azatyrosine; baccatin III derivatives; balanol; batimastat, BCR/ABL antagonists; benzochlorins; benzoylstaursporine; beta lactam derivatives; betaalethine; betaclamycin B; betulinic acid; bFGF inhibitor, bicalutamide; bisantrene; bisazindinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthrequinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocanmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarbine; fenretinido; filgrastim; frnasteride; flavopiridol; flezelastine; fluasterone; fludarabine; fluorodaunorunicin hydrochloride; torfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists, interferons; interleukins; iobonguane; iododoxorubicin; ipomeanol, 4; trinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole liarozole; linear polyamine analogue; lipophilicadisaccharide peptide; lipophilic platinum compounds; lissoclinamide-7; lobaplatin, lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosplioryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulator; nitroxide antioxidant; nitrullyn; O6-benzylguanine; octreotide; okicenone; oligonucleotides; onapristone; orldarisetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaepergase; peldesine; pentosan polysulfate sodium; pentostatin; pentrozole; perflubron; perfosfamide; perrillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum comprex; platinum compounds; platinum-triamine coil iplex; porfimer sodium; portiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purino mucleoside phosphorylast inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitor; ras-GAP inhibitor, retalliptine demethylated; rhenium Re186 etidronate; rhizoxin; ribozymes; RII retinamide;

rogletimide; rohitukine; romurtide; roquinimex; rubiginone B1; ruboxyl; safingol; saintopin; SarCNU; sarcophytol A; sargramostim, Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmonine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erytrocyte gene therapy; velaresol; venom, anti-venom, veramine; verdins; verteporfin; vinorelbine; vinxaltine; vitaxin; vorozole; zanoterone; zeniplatin; zilascorb; zinostatin stimalamer, immunostimulating drugs or therapeutic agents, their metabolites, salts and derivatives thereof, and combinations thereof.

In some embodiments, these agents can be used in conjunction with other cancer therapies. In some embodiments, one or more of the compounds are used with other anticancer drugs, such as, for example gemcitabine and lapatinib, irradiation to sensitize cancer stem cells, and/or surgical intervention. Other anticancer drugs that can be combined with the compounds as described herein include, for example, Abraxane, Aldara, Alimta, Aprepitant, Arimidex, Aromasin, Arranon, Arsenic Trioxide, Avastin, Bevacizumab, Bexarotene, Bortezomib, Cetuximab, Clofarabine, Clofarex, Clolar, Dacogen, Dasatinib, Ellence, Eloxatin, Emend, Erlotinib, Faslodex, Femara, Fulvestrant, Gefitinib, Gemtuzumab Ozogamicin, Gemzar, Gleevec, Herceptin, Hycamtin, Imatinib Mesylate, Iressa, Kepivance, Lenalidomide, Levulan, Methazolastone, Mylosar, Mylotarg, Nanoparticle Paclitaxel, Nelarabine, Nexavar, Nolvadex, Oncaspar, Oxaliplatin, Paclitaxel, Paclitaxel Albumin-stabilized Nanoparticle Formulation, Palifermin, Panitumumab, Pegaspargase, Pemetrexed Disodium, Platinol-AQ, Platinol, Revlimid, Rituxan, Sclerosol Intrapleural Aerosol, Sorafenib Tosylate, Sprycel, Sunitinib Malate, Sutent, Synovir, Tamoxifen, Tarceva, Targretin, Taxol, Taxotere, Temodar, Temozolomide, Thalomid, Thalidomide, Topotecan Hydrochloride, Trastuzumab, Trisenox, Vectibix, Velcade, Vidaza, Vorinostat, Xeloda, Zoledronic Acid, Zolinza, Zometa, doxorubicin, adriamycin, bleomycin, daunorubicin, dactinomycin, epirubicin, idarubicin, mitoxantrone, valrubicin, hydroxyurea, mitomycin, fluorouracil, 5-FU, methotrexate, floxuridine, interferon alpha-2b, glutamic acid, plicamycin, 6-thioguanine, aminopterin, pemetrexed, raltitrexed, cladribine, clofarabine, fludarabine, mercaptopurine, pentostatin, capecitabine, cytarabine, carmustine, BCNU, lomustine, CCNU, cytosine arabinoside, cyclophosphamide, estramustine, hydroxyurea, procarbazine, mitomycin, busulfan, medroxyprogesterone, estramustine phosphate sodium, ethinyl estradiol, estradiol, megestrol acetate, methyltestosterone, diethylstilbestrol diphosphate, chlorotrianisene, testolactone, mephalen, mechlorethamine, chlorambucil, chlormethine, ifosfamide, bethamethasone sodium phosphate, dicarbazine, asparaginase, mitotane, vincristine, vinblastine, etoposide, teniposide, Topotecan, IFN-gamma, irinotecan, campto, irinotecan analogs, carmustine, fotemustine, lomustine, streptozocin, carboplatin, oxaliplatin, BBR3464, busulfan, dacarbazine, mechlorethamine, procarbazine, thioTEPA, uramustine, vindesine, vinorelbine, alemtuzumab, tositumomab, methyl aminolevulinate, porfimer, verteporfin, lapatinib, nilotinib, vandetanib, ZD6474, alitretinoin, altretamine, amsacrine, anagrelide, denileukin diftitox, estramustine, hydroxycarbamide, masoprocol, mitotane, tretinoin, or other anticancer drugs, including, for example, antibiotic derivatives, cytotoxic agents, angiogenesis inhibitors, hormones or hormone derivatives, nitrogen mustards and derivatives, steroids and combinations, and antimetbolites. Other chemotherapeutic drugs include Notch inhibitor, TGFbeta inhibitor, Pdx1 inhibitor, Oct4 inhibitor, Sox2 inhibitor, Sox4 inhibitor, KLF4 inhibitor inhibitor, TCF/LEF inhibitor, Nanog inhibitor, AKT inhibitor, FLT3 kinase inhibitor, PI3 Kinase inhibitor, PI3 kinase/mTOR (dual inhibitor), PI3K/AKT pathway inhibitor, Hedgehog pathway inhibitor, Gli inhibitor, Smoothened inhibitor, JAK/STAT pathway inhibitor, Ras/MEK/ERK pathway inhibitor, and BRAF inhibitor. In further particular aspects of the invention, an anticancer drug comprises two or more of the foregoing anticancer drugs.

Suitable compositions and dosage forms also include tablets, capsules, nanoparticles, caplets, gel caps, troches, dispersions, suspensions, solutions, syrups, transdermal patches, gels, powders, magmas, lozenges, creams, pastes, plasters, lotions, discs, suppositories, liquid sprays for nasal or oral administration, dry powder or aerosolized formulations for inhalation, and the like.

Many engineered multifunctional nanoparticles can be used as pharmaceutical drug carriers, including nano-emulsions, dendrimers, nano-gold, liposomes, drug-carrier conjugates, antibody-drug complexes, and magnetic nanoparticles, are primarily based on unique assemblies of synthetic or biological components, including but not limited to synthetic polymers, metal ions, oils, and lipids as their building blocks.

This nano-assembly includes imaging molecules, a payload of drugs, ligands for site-specific targeting, and a destabilizing lipid that allows for on-demand drug release at the desired site, as well as sensors that probe the efficacy of the drug in real time. Some widely examined nano-carriers aimed at delivering DNA, pharmaceuticals, and/or imaging agents include dendrimers, nano-gold shells, nano-emulsions, drug-polymer conjugates, drug-antibody conjugates and quantum dots. Each of these is based on unique properties of the structural components used in fabricating the delivery vehicle and relies on self-assembly of the structural motifs, while accommodating the pharmaceutical agent and the targeting ligand. A limited number of the drug-loaded nanoparticles are successful for their clinical applications. An important parameter of the delivery vehicle pertains to low or no toxicity of the carrier itself either in vivo or in the environment as a by-product.

Oral dosage forms are preferred for those therapeutic agents that are orally active, and include tablets, capsules, nanoparticles, caplets, solutions, suspensions and/or syrups, and may also comprise a plurality of granules, beads, powders or pellets that may or may not be encapsulated. Such dosage forms can be prepared using conventional methods known to those in the field of pharmaceutical formulation and described in the pertinent texts, e.g., in *Remington: The Science and Practice of Pharmacy,* 20th Edition, Gennaro, A. R., Ed. (Lippincott, Williams and Wilkins, 2000).

Tablets and capsules represent the most convenient oral dosage forms, in which case solid pharmaceutical carriers are employed. Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), tablets prepared for oral administration will generally contain other materials such as binders, diluents, lubricants, disintegrants, fillers, stabilizers, surfactants, coloring agents, imaging agent, and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the active agent-containing composition may be encapsulated in the form of a liquid or solid (including particulates such as granules, beads, nanoparticles, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition, and must be suitable for ingestion.

Solid dosage forms, whether tablets, capsules, nanoparticles, caplets, or particulates, may, if desired, be coated so as to provide for delayed release. Dosage forms with delayed release coatings may be manufactured using standard coating procedures and equipment. Such procedures are known to those skilled in the art and described in the pertinent texts, e.g., in Remington, supra. Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Parenteral administration, if used, is generally characterized by injection, including intramuscular, intraperitoneal, intravenous (IV) and subcutaneous injection. Injectable formulations can be prepared in conventional forms, either as liquid solutions or suspensions, solid forms suitable for solution or suspension in liquid prior to injection, or as emulsions. In some embodiments, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. In some embodiments, the formulation for parenteral administration is a controlled release formulation, such as delayed or sustained release.

Any of the active agents may be administered in the form of a salt, ester, amide, prodrug, active metabolite, derivative, or the like, provided that the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base using conventional methodology, and involves reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are salts prepared with organic acids. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Targeted drug delivery, sometimes called smart drug delivery, is a method of delivering medication to a patient in a manner that increases the concentration of the medication in some parts of the body relative to others. The goal of a targeted drug delivery system is to prolong, localize, target and have a protected drug interaction with the diseased tissue. The conventional drug delivery system is the absorption of the drug across a biological membrane, whereas the targeted release system is when the drug is released in a dosage form. The advantages to the targeted release system is the reduction in the frequency of the dosages taken by the patient, having a more uniform effect of the drug, reduction of drug side effects, and reduced fluctuation in circulating drug levels. Drugs can be delivered using liposomes, micelles, nanoparticles, and dendrimers, polymers, biodegradable particles, and artificial DNA nanostructure. Nanoparticles or nanostructures can be conjugated with targeting antibodies, peptides and proteins, and can carry imaging agent(s). Particles (diameter 80 to 600 nM) comprised of the polymer poly(lactic-co-glycolic acid) (PLGA) are widely studied as therapeutic delivery vehicles because they are biodegradable and biocompatible. PLGA particles also offer considerable flexibility in choosing a route of delivery because they have proven to be effective when injected intramuscularly, when delivered via inhalation, and have been recently indicated for oral delivery of drugs and antigens.

To facilitate a better understanding of the present invention, the following examples of certain aspects of some embodiments are given. In no way should the following examples be read to limit, or define, the entire scope of the invention.

REFERENCES

1. Ponti, D., et al., Breast cancer stem cells: an overview. Eur J Cancer, 2006. 42(9): p. 1219-24.
2. Cariati, M. and A. D. Purushotham, Stem cells and breast cancer. Histopathology, 2008. 52(1): p. 99-107.
3. Gonzalez-Sarmiento, R. and J. Perez-Losada, Breast cancer, a stem cell disease. Curr Stem Cell Res Ther, 2008. 3(1): p. 55-65.
4. Lawson, J. C., G. L. Blatch, and A. L. Edkins, Cancer stem cells in breast cancer and metastasis. Breast Cancer Res Treat, 2009. 118(2): p. 241-54.
5. Liu, S., G. Dontu, and M. S. Wicha, Mammary stem cells, self-renewal pathways, and carcinogenesis. Breast Cancer Res, 2005. 7(3): p. 86-95.
6. Lynch, M. D., M. Cariati, and A. D. Purushotham, Breast cancer, stem cells and prospects for therapy. Breast Cancer Res, 2006. 8(3): p. 211.
7. Siegel, R., D. Naishadham, and A. Jemal, Cancer statistics, 2013. CA Cancer J Clin, 2013. 63(1): p. 11-30.
8. Warshaw, A. L. and C. Fernandez-del Castillo, Pancreatic carcinoma. N Engl J Med, 1992. 326(7): p. 455-65.
9. Magee, C. J., P. Ghaneh, and J. P. Neoptolemos, Surgical and medical therapy for pancreatic carcinoma. Best Pract Res Clin Gastroenterol, 2002. 16(3): p. 435-55.
10. Bardeesy, N. and R. A. DePinho, Pancreatic cancer biology and genetics. Nat Rev Cancer, 2002. 2(12): p. 897-909.
11. Nieto, J., M. L. Grossbard, and P. Kozuch, Metastatic pancreatic cancer 2008: is the glass less empty? Oncologist, 2008. 13(5): p. 562-76.
12. Huang, M., et al., Embelin Suppresses Growth of Human Pancreatic Cancer Xenografts, and Pancreatic Cancer Cells Isolated from KrasG12D Mice by Inhibiting Akt and Sonic Hedgehog Pathways. PLoS ONE, 2014. 9(4): p. e92161.
13. Nalls, D., et al., Targeting epigenetic regulation of miR-34a for treatment of pancreatic cancer by inhibition of pancreatic cancer stem cells. PLoS One, 2011. 6(8): p. e24099.

14. Shankar, S., et al., Resveratrol inhibits pancreatic cancer stem cell characteristics in human and KrasG12D transgenic mice by inhibiting pluripotency maintaining factors and epithelial-mesenchymal transition. PLoS ONE, 2011. 6(1): p. e16530.
15. Tang, S. N., et al., Inhibition of sonic hedgehog pathway and pluripotency maintaining factors regulate human pancreatic cancer stem cell characteristics. Int J Cancer, 2012. 131(1): p. 30-40.
16. Dobreva, G., J. Dambacher, and R. Grosschedl, SUMO modification of a novel MAR-binding protein, SATB2, modulates immunoglobulin mu gene expression. Genes Dev, 2003. 17(24): p. 3048-61.
17. Cai, S., C. C. Lee, and T. Kohwi-Shigematsu, SATB1 packages densely looped, transcriptionally active chromatin for coordinated expression of cytokine genes. Nat Genet, 2006. 38(11): p. 1278-88.
18. Dobreva, G., et al., SATB2 is a multifunctional determinant of craniofacial patterning and osteoblast differentiation. Cell, 2006. 125(5): p. 971-86.
19. Britanova, O., et al., Novel transcription factor Satb2 interacts with matrix attachment region DNA elements in a tissue-specific manner and demonstrates cell-type-dependent expression in the developing mouse CNS. Eur J Neurosci, 2005. 21(3): p. 658-68.
20. Gyorgy, A. B., et al., SATB2 interacts with chromatin-remodeling molecules in differentiating cortical neurons. Eur J Neurosci, 2008. 27(4): p. 865-73.
21. Notani, D., et al., Global regulator SATB1 recruits beta-catenin and regulates T(H)2 differentiation in Wnt-dependent manner. PLoS Biol, 2010. 8(1): p. e1000296.
22. Britanova, O., et al., Satb2 is a postmitotic determinant for upper-layer neuron specification in the neocortex. Neuron, 2008. 57(3): p. 378-92.
23. Magnusson, K., et al., SATB2 in combination with cytokeratin 20 identifies over 95% of all colorectal carcinomas. Am J Surg Pathol, 2011. 35(7): p. 937-48.
24. Patani, N., et al., The mRNA expression of SATB1 and SATB2 in human breast cancer. Cancer Cell Int, 2009. 9: p. 18.
25. Javed, S. and S. E. Langley, Importance of HOX genes in normal prostate gland formation, prostate cancer development and its early detection. BJU Int, 2014. 113(4): p. 535-40.
26. Wallen, A. and T. Perlmann, Transcriptional control of dopamine neuron development. Ann N Y Acad Sci, 2003. 991: p. 48-60.
27. Chung, Y. J., et al., Oxidative stress leads to increased mutation frequency in a murine model of myelodysplastic syndrome. Leuk Res, 2014. 38(1): p. 95-102.
28. McGrath, S. E., et al., EN2: a novel prostate cancer biomarker. Biomark Med, 2013. 7(6): p. 893-901.
29. Sengupta, N., E. Siddiqui, and F. H. Mumtaz, Cancers of the bladder. J R Soc Promot Health, 2004. 124(5): p. 228-9.
30. Killick, E., et al., Role of Engrailed-2 (EN2) as a prostate cancer detection biomarker in genetically high risk men. Sci Rep, 2013. 3: p. 2059.
31. Marszall, M. P., et al., Engrailed-2 protein as a potential urinary prostate cancer biomarker: a comparison study before and after digital rectal examination. Eur J Cancer Prev, 2015. 24(1): p. 51-6.
32. Morgan, R., et al., Engrailed-2 (EN2): a tumor specific urinary biomarker for the early diagnosis of prostate cancer. Clin Cancer Res, 2011. 17(5): p. 1090-8.
33. Morgan, R., et al., Expression of Engrailed-2 (EN2) protein in bladder cancer and its potential utility as a urinary diagnostic biomarker. Eur J Cancer, 2013. 49(9): p. 2214-22.
34. Pandha, H., et al., Urinary engrailed-2 (EN2) levels predict tumour volume in men undergoing radical prostatectomy for prostate cancer. BJU Int, 2012. 110(6 Pt B): p. E287-92.

What is claimed is:

1. A method for treating or preventing cancer in a subject, comprising administering to the subject a pharmaceutical composition comprising an effective amount of at least one agent that inhibits at least one of EN2 expression, EN2 transcriptional activity, SATB2 expression, or SATB2 transcriptional activity, wherein SATB2 and EN2 are highly expressed in the cancer, and the at least one agent is a small organic molecule represented by a compound having the chemical structure of

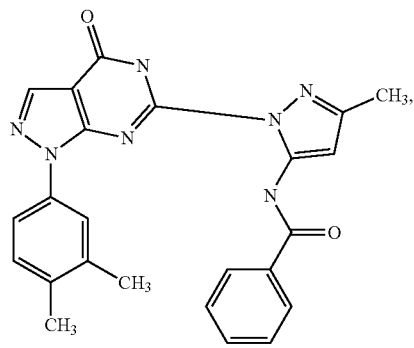

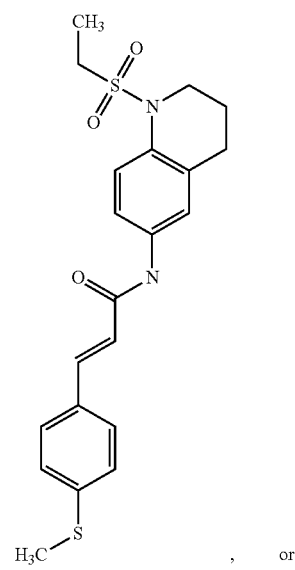

, or

-continued

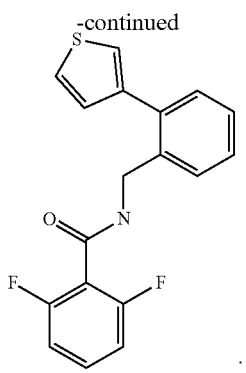

2. The method of claim 1, wherein the at least one agent comprises a targeting moiety capable of binding to a surface of a cancer cell, wherein the targeting moiety is selected from the group consisting of aptamers, peptides, biodegradable materials, antibody-derived epitope binding domains, cellular ligands, and combination thereof.

3. The method of claim 1, wherein the method further comprises:
   determining EN2 and/or SATB2 expression level of said subject.

4. The method of claim 1, wherein the at least one agent is administered in nanoparticles.

5. The method of claim 1, wherein the at least one agent is administered to the subject in combination with one or more chemotherapeutic drugs or radiation for treatment and prevention of cancer.

\* \* \* \* \*